United States Patent [19]

Haertle et al.

[11] Patent Number: 4,997,926
[45] Date of Patent: Mar. 5, 1991

[54] DEAMINASE-STABLE ANTI-RETROVIRAL 2-HALO-2',3'-DIDEOXY

[75] Inventors: Thomasz Haertle, Nantes Cédex, France; Dennis A. Carson, Del Mar, Calif.

[73] Assignee: Scripps Clinic and Research Foundation, La Jolla, Calif.

[21] Appl. No.: 121,950

[22] Filed: Nov. 18, 1987

[51] Int. Cl.$^5$ .................. C07H 19/16; C07H 19/173
[52] U.S. Cl. ........................................ 536/26; 536/24
[58] Field of Search ............... 536/23, 24, 26; 514/45, 514/46

[56] References Cited

PUBLICATIONS

Broder, "AIDS, Modern Concepts and Therapeutic Challenges", Dekken, 1987, pp. 303-333, particularly pp. 308-309.
Dahlberg et al., Proc. Nat. Acad. Sci., U.S.A., vol. 84, pp. 2469-2473, 1987.
Kowollik et al., Chem. Abstr., vol. 99, 158785p, 1983.
Mitsuya et al., Proc. Nat. Acad. Sci., U.S.A., vol. 83, pp. 1911-1915, 1986.
Christensen et al., J. Med. Chem., vol. 15, pp. 735-739, 1972.
Waqar et al., J. Cell Physiology, vol. 121, pp. 402-408, 1984.
Mitsuya et al. (II), "Protection of T Cells Against Infectivity and Cytopathic Effect of HTLV-III In Vitro," in Retroviruses in Human Lymphoma/Leukemia, Miwa et al. eds., Japan Sc. Soc. Press, Tokyo, 1985, see pp. 277-288.
Sandstrom et al., Drugs, vol. 34, pp. 372-390, (1987).
Loupe, "FDA Broadens Use of Unproven AIDS Drug", Science News, p. 231, (Oct. 7, 1989).
Frederiksen et al., Cancer Res., 2:125-130, (1962).
Carson et al., Proc. Natl. Acad. Sci., U.S.A., 81:2232-2236, (1984).
Haertle et al., J. Biol. Chem., 263:5870-5875, (1988).

Primary Examiner—John W. Rollins
Assistant Examiner—L. Eric Crane
Attorney, Agent, or Firm—Dressler, Goldsmith, Shore, Sutker & Milnamow, Ltd.

[57] ABSTRACT

Adenine deaminase-stable adenine derivatives bonded 9,1' to a furanosidyl ring containing a 5'-hydroxyl group are described. These compounds are useful in a method of inhibiting replication of reverse transcriptase-dependent viruses.

5 Claims, 5 Drawing Sheets

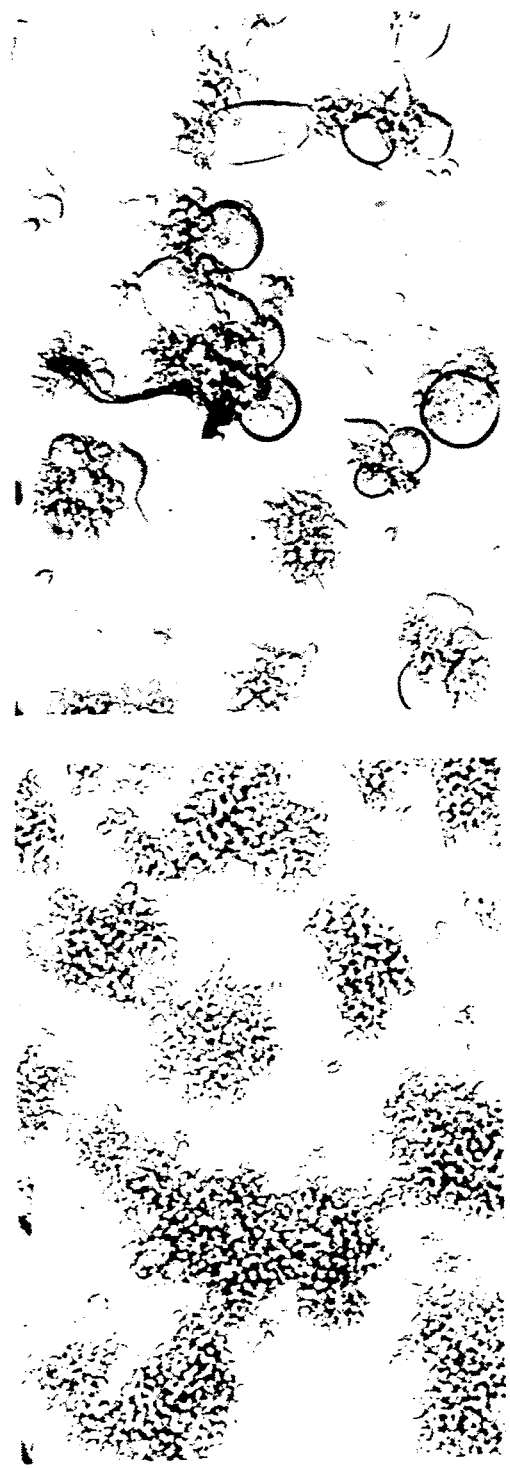
FIG.1B POSITIVE CONTROL NO NUCLEOSIDE
FIG.1A NEGATIVE CONTROL NO VIRUS

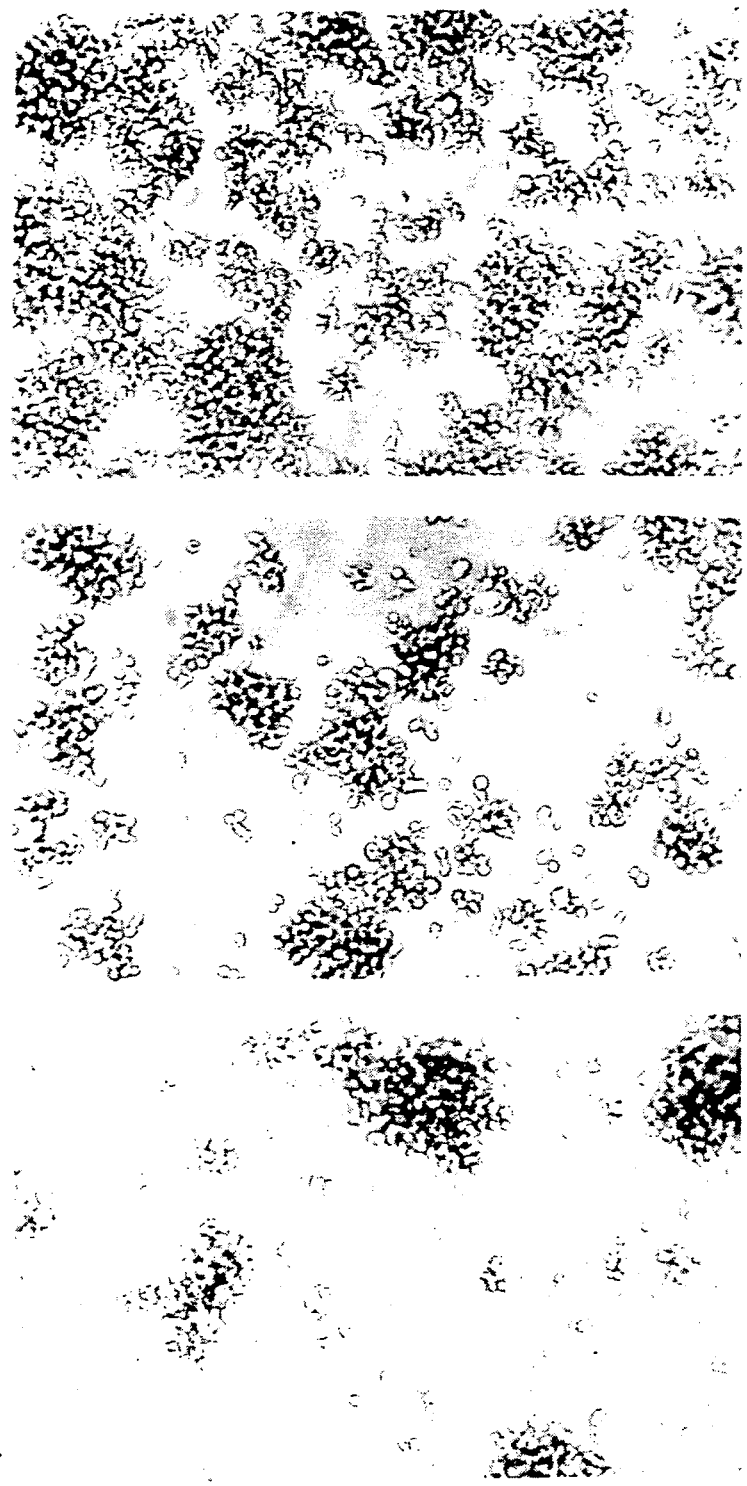
FIG.1E 2-BROMO-2',3'-DIDEOXYADENOSINE
FIG.1D 2-CHLORO-2',3'-DIDEOXYADENOSINE
FIG.1C 2-FLUORO-2',3'-DIDEOXYADENOSINE

DEAMINASE-STABLE ANTI-RETROVIRAL 2-HALO-2',3'-DIDEOXY

This invention was made with support from the United States Government, and the United States Government has certain rights in the invention

TECHNICAL FIELD

The present invention relates to nucleosides that are active against retroviruses, and particularly to adenosine derivatives that are stable to the enzyme adenosine deaminase.

BACKGROUND ART

Reverse transcriptase-dependent viruses (RTDV) are those viruses whose genomes encode and transcribe an enzyme known as reverse transcriptase [ribonucleic acid (RNA)-dependent deoxyribonucleic acid (DNA) polymerase or RDDP]. Illustrative of such viruses are the retroviruses or RNA tumor viruses, e.g., human T-lymphotropic viruses (HTLV), human immunodeficiency viruses (HIV), feline leukemia virus (FeLV), Moloney murine leukemia virus (Mo-MuLV), and the like, plant viruses, e.g., cauliflower mosaic virus (a double stranded DNA virus that encodes an enzyme which, when expressed in vitro, also has RDDP activity substantially the same as that of Mo-MuLV) and the like, hepatitis B virus, and others. See, for example, Varmus (1983), *Nature,* 304:116–117, Varmus et al., "Replication of Retroviruses," in *RNA Tumor Viruses,* Weiss et al., eds., Cold Spring Harbor Laboratories, p 75–134 (1985) and Toh et al. (1983) *Nature,* 305:827–829.

Synthesis of DNA complementary to viral RNA is thought to be required for both retroviral integration into host DNA and for the generation of new virions. For this reason, the HIV-encoded reverse transcriptase is a logical target for the development of agent for the treatment of patients with the acquired immunodeficiency syndrome [De Clercq et al. (1986) *J. Med. Chem.,* 29:1561–1569], and with other diseases of retroviral origin.

Mitsuya et al. (1985) *Proc. Natl. Acad. Sci. USA,* 82:7006–7100 reported 3'-azido-3'-deoxythymidine (AZT) blocked the replication of HIV in cultured human T lymphoblasts, and inhibited the cytopathic effects of the virus. AZT was presumably phosphorylated by the T cells and converted to the 5'-triphosphate derivative. That derivative was reported by those authors to be an inhibitor of HIV reverse transcriptase activity.

Yarchoan et al. (1986) *Lancet,* i:575–580, administered AZT to patients with AIDS or AIDS-related disease complexes. The drug was reportedly well tolerated and crossed the blood/brain barrier.

Recently, Mitsuya et al. (1986) *Proc. Natl. Acad. Sci. USA,* 83:1911–1915 reported that the 2',3'-dideoxynucleoside derivatives of adenosine, guanosine, inosine, cytidine and thymidine also inhibited the infectivity and cytopathic effect of HIV in vitro at concentrations from 10–20 fold less than those that blocked the proliferation of uninfected T cells. These compounds were reported to be relatively non-toxic towards host T cells; a surprising finding. The adenosine and cytidine derivatives were reported to be more potent than the guanosine and inosine derivatives.

The 2',3'-dideoxynucleosides are phosphorylated at the 5'-position in T cells to form the 5'-nucleotide triphosphate derivatives. Those derivatives are well known to be substrates for reverse transcriptase molecules. Ono et al. (1986) *Biochem. Biophys. Res. Comm.,* 2:498–507.

Those 2',3'-dideoxynucleoside 5'-triphosphates are also utilized by mammalian DNA polymerases beta and gamma. Waquar et al., (1984) *J. Cell. Physiol.,* 121:402–408. They are, however, poor substrates for DNA polymerase-alpha, the main enzyme responsible for both repair and replicative DNA synthesis in human lymphocytes. In part, these properties may explain the selective anti-HIV activity of the 2',3'-dideoxy-nucelosides.

It is presumed that AZT 5'-triphosphate and 2',3'-dideoxy-5'-triphosphate derivatives are incorporated into a growing RNA or DNA chain. However, lacking a 3'-hydroxyl group that is necessary to form a 3',5'-phosphodiester group, the growing RNA or DNA (polynucleotide) terminates, and thereby, presumably, inhibits HIV replication and infection.

The antiviral activity of AZT probably requires the phosphorylation of the nucleoside by thymidine kinase. This cell cycle-dependent enzyme has very low activity in human peripheral blood lymphocytes, unless the cells are stimulated to divide by a mitogen or antigen. Pegoraro et al. (1971) *Exp. Cell Res.,* 66:283–290. For that reason, it is unlikely that substantial amounts of 3'-azido-3'-deoxythymidine 5'-phosphate accumulates in normal human peripheral blood T cells.

Most in vitro assays for HIV infection of normal T cells require lymphocyte activation by an antigen or mitogen. Burre-Sinoussi et al. (1983) *Science,* 220:868–871; Povovic et al. (1984) *Science* 224:497–500; Levy et al. (1984) *Science,* 225:840–842; Klatzmann et al. *Science,* 225:59–63; and Dalgleish et al. (1984) *Nature,* 312:763–766. Although such activation may be required for before viral protein can be detected due to the relatively low in vitro pathogenicity of the virus, it is thought that at least some normal peripheral blood T lymphocytes are infected by the virus since those cells express the T4 (CD4) viral receptor. Thus, AZT and other anti-viral nucleoside substrates for thymidine kinase may not totally prevent the spread of HIV infection to the residual normal T lymphocytes that circulate in infected patients.

Recent reports indicate that HIV infects macrophages and monocytes in addition to T cells. Levy et al. (1985) *Virology,* 147:441–448; Gartner et al (1986) *Science,* 233:215–219; and Wiley et al. (1986) *Proc. Natl. Acad. Sci. USA,* 83:7089–7093. Monocytes and macrophages have minimal or no thymidine kinase activity, although such cells do possess deoxycytidine kinase activity [Carson et al. (1977) *Proc. Natl. Acad. Sci. USA,* 74:5677–5681] that can phosphorylate 2',3'-dideoxycytidine (ddC). Monocytes and macrophages also appear to lack deoxycytidine kinase activity. Chan et al. (1982) *J. Cell Physiol.,* 111:28–32.

Thus, in normal T cells, one would expect dideoxycytidine to be more effective than AZT since the former nucleoside can be phosphorylated by intracellular enzymes whereas the latter nucleoside cannot. Neither nucleoside can be expected to be phosphorylated by monocytes and macrophages. It is thought that the lack of intracellular phosphorylation and subsequent incorporation and chain termination in monocytes and macrophages contributes to the failure of nucleosides like AZT to eradicate HIV from the patient's blood.

Preliminary studies by the present inventors and their co-workers indicate that human monocyte derived macrophages (MDM) exhibit about one-tenth to about one-fourth the nucleoside kinase activity of CEM T lymphoblasts toward uridine, deoxycytidine and thymidine, and about two-thirds the adenosine kinase activity of CEM cells. In addition, that adenosine kinase activity of MDM cells is at least about 10-fold higher than any of the other kinase activities. Those studies also indicated relatively low levels of nucleoside phosphorylation using AZT, ddC and 2',3'-dideoxyadenosine (ddA) in intact CEM T lymphoblasts and still lower levels with the MDM.

The ability of AZT, ddC and ddA to inhibit synthesis of the p24 (gag) antigen of HIV in CEM and MDM cells was also examined. For CEM cells, the results for all three compounds were similar to those discussed in Mitsuya et al. (1987) *Nature*, 325:773–778 with ddC providing the most inhibitory effect at the lowest concentration, followed by AZT, followed by ddA in a 3-day assay. Using the same concentrations (0.1–100 uM) in a similar 3-day assay, none of those compounds provided any inhibition of p24 (gag) production from MDM cells.

The above results explain in part the observations made in clinical trials with AZT. Those results, in part, have shown that treatment of patients with AIDS or AIDS-related complex with AZT has resulted in elevation of CD4 (T4) peripheral blood cell counts, restoration of cutaneous delayed hypersensitivity, and reduction of the rate of opportunistic infections and death; results that can be related to the effect of AZT on T cells.

However, AZT had no effect on virus isolation rates from peripheral blood cells. That result suggests that a subset of infected cells persists that represents a reservoir of continuing viral replication, and with the above work with MDM cells, indicates that macrophages constitute at least a portion of that in vivo reservoir.

That AZT and ddC were not effective in the monocyte assay was not surprising in view of the before-mentioned relatively low kinase activity for the related 2'-deoxy nucleosides found in MDM cells. The similar finding as to ddA is more puzzling in view of the much greater adenosine kinase activity of MDM cells.

Although MDM cells produced lower amounts of dideoxynucleoside 5'-triphosphates than did T lymphoblasts over a four hour time period, the magnitude of that difference cannot account entirely for the failure of these nucleosides having potent effects in T cells to inhibit HIV replication in MDM cells. Other factors such as nucleotide pools, the initial rate of nucleotide formation compared to the time of reverse transcription, and adenine deaminase activity may also influence the anti-HIV activity of those compounds.

As noted before, 2',3'-dideoxyadenosine (ddA) inhibits in vitro infectivity and cytopathic effects of HIV. Mitsuya et al. (1986) *Proc. Natl. Acad. Sci. USA*, 83:1911–1915. However, ddA is a known substrate for adenosine deaminase (also known as adenosine aminohydrolase, EC 3.5.4.4), which converts the compound to 2',3'-dideoxyinosine (ddI). Frederiksen (1966) *Arch. Biocyem. Biophys.*, 113:383–388. Adenosine deaminase levels in the blood of AIDS patients are relatively high compared to normal persons. Thus, in vivo, ddA would be expected to have little effect on HIV due to the action of endogenous adenine deaminase.

On the other hand, several 2-substituted adenosine derivatives have been reported not to be deaminated by adenosine deaminase. For example, Coddington (1965) *Biochim. Biophys Acta*, 99:442–451 reported that deoxyadenosine-1-N-oxide, as well as 2-hydroxy, 2-methyl, 2-chloro, 2-acetamido and 2-methylthio adenosines were neither substrates nor inhibitors for adenosine deaminase. Montgomery, in *Nucleosides, Nucleotides, and Their Biological Applications*, Rideout et al eds., Academic Press, New York, p 19 (1983) provides a table of comparative Km and Vmax data for the deamination of adenosine, 2-halo-adenosines, 2-halo-deoxyadenosines and 2-fluoro-arabinoadenosine; that also indicate that those 2-halo, adenosines derivatives are poor substrates for the enzyme relative to adenine itself. Stoeckler et al. (1982) *Biochem. Pharm.*, 31:1723–1728 reported that the 2'-deoxy-2'-azidoribosyl and arabinosyl adenine derivatives were substrates for human erythrocytic adenosine deaminase, whereas work of others indicated 2-fluoroadenosine to have negligible activity with adenosine deaminase.

Both dividing and resting (normal) human T lymphocytes contain especially high levels of deoxycytidine kinase, a nucleoside phosphorylating enzyme for which both deoxyguanosine and deoxyadenosine are alternative substrates. Carson et al. (1977) *Proc. Natl. Acad. Sci. USA*, 74:5677–5681. Deoxyadenosine is also a substrate for adenosine kinase [Hershfield et al. (1982) *J. Biol. Chem.*, 257:6380–6386], an enzyme also present in T lymphocytes. Additional substrates for adenosine kinase including adenosine-1-N-oxide, arabinofuranosyladenine, xylofuranosyladenine, 2'-amino-2',3'-dideoxyadenosine, 2-fluoroadenosine and 3-deoxyadenosine are reported by Lindberg et al., (1967) *J. Biol. Chem.*, 242:350–356. Lindberg et al. also reported that a number of compounds including 2'-deoxyadenosine-1-N-oxide, 3'-deoxyadenosine-1-N-oxide and 2',3'-dideoxyadenosine were neither substrates nor inhibitors for the enzyme.

T lymphocytes also contain relatively low levels of cytoplasmic 5'-nucleotidase, an enzyme that returns 5'-nucleotides to their respective nucleoside forms. As a result of the relatively high 5'-phosphorylating activity and low dephosphorylating activity of T lymphocytes, as well as the difficulty of ionically charged compounds such as nucleotides in traversing cellular membranes, human T lymphocytes tend to sequester deoxyadenosine 5'-triphosphate and deoxyguanosine 5'-triphosphate when exposed to relatively low external concentrations of the respective nucleosides.

Norman human T lymphocytes form little thymidine 5'-triphosphate when exposed to exogenous thymidine. In contrast, normal human T cells accumulate substantial amounts of deoxyadenosine 5'-triphosphate when incubated in medium supplemented with deoxyadenosine and an adenosine deaminase inhibitor. Seto et al. (1985) *J. Clin. Invest.*, 75:377–383; and Kefford et al. (1982) *Cancer Res.*, 42:324–330.

Deoxyadenosine 5-triphosphate causes the secretion of DNA single-strand breaks in resting, normal T cells, presumably by inhibiting DNA polymerase-alpha. Seto et al. (1985) *J. Clin. Invest.*, 75:377–383; Seto et al. (1986) *J. Immunol.*, 136:2839–2843. Such DNA breaks trigger a programmed "suicide" response in the T cells that is associated with a lethal depletion of NAD and ATP pools, during exhaustive poly(ADP-ribose) synthesis.

One report suggests that 2',3'-dideoxynucleoside 5'-triphosphates are not substrates for DNA polymerase-alpha Edenberg et al. (1978) *J. Biol. Chem.*, 253:3273-3280. Preliminary work from our own laboratories indicates that such compounds should not inhibit DNA repair in human normal peripheral blood lymphocytes.

Work directed toward the inhibition of growth of human malignant T cell lines in our own laboratories examined the resistance of adenine derivatives to deamination by adenosine deaminase and the toxicity of resistant derivatives toward human T and B lymphoblastoid cell lines. The most potent agent, on a molar basis, was found to be 2-chloro-2'-deoxyadenosine.

That compound was able to inhibit growth of human malignant T cell lines at concentrations of 0.001-0.03 micromolar (uM). Cell lines derived from solid tissues, e.g., Hela cells and normal fibroblasts, were found to be about 100-times more resistant to that adenine derivative. 2-Chloro-2'-deoxyadenosine can be toxic toward fresh T cells, but has no discernable effects on mature granulocytes. Carson et al. (1983) *Blood*, 62:737-743.

2-Chloro-2'-deoxyadenosine is phosphorylated by non-dividing (normal) human peripheral blood lymphocytes and is converted to the 5'-triphosphate. This adenine derivative is not catabolized significantly by intact human cells or cell extracts, and is phosphorylated efficiently by T lymphocytes. Carson et al. (1980) *Proc. Natl. Acad. Sci. USA*, 77:6865-6869.

Phase 1 studies on humans showed infusion of increasing doses of that 2-chloro-2'-deoxyadenosine [0.1-0.5 milligrams per kilogram of body weight per day (mg/kg/day)] yielded increasing plasma concentrations of the drug [10-50 nanomolar (nM)]. Those infusions indicated that that drug was well tolerated and did not induce nausea, vomiting or fever. The dose-limiting toxicity was bone marrow suppression, which usually occurred at doses greater than about 0.2 mg/kg/day or at plasma levels of greater than about 20 nM.

Other studies, Montgomery et al. (1960) *J. Am. Chem. Soc.*, 82:463-468, indicated that 2-fluoroadenosine exhibits a relatively high degree of cytotoxicity. Those workers reported that C57 black mice implanted with Adenocarcinoma 755 (Ad755) could tolerate only about 1 milligram per kilogram of body weight. 2-Fluoroadenosine was found to be inactive at that level against Ad755 as well as leukemia L1210 and the Erlich ascites tumor.

In work recently published [Herdewijn et al. (1987) *J. Med. Chem.*, 30:1270-1278], the activity against HLV and the toxicity in T cells are reported for a number of nucleosides. Among the compounds discussed were ddA, 3'-fluoro-ddA, and 3'-azido-ddA.

Concentrations providing a 50 percent protection level of HIV-infected ATH8 cells against the cytopathic effect of HIV were reported to be 2.7, 8 and 4.8 micromolar, respectively. Doses required to reduce the viability of normal, uninfected ATH8 cells by 50 percent were determined to be more than 500, more than 250 and 27 micromolar, respectively.

An adenine derivative that is: (a) capable of traversing the cellular membrane from the medium, (b) capable of being phosphorylated to the 5'-triphosphate once inside a T cell, (c) substantially free from deamination, (d) a non-inhibitor for DNA polymerase-alpha, (e) capable of inhibiting retroviral replication such as by terminating a growing RNA or DNA chain, and (f) relatively non-toxic to the retrovirally-infected cells and generally to the host animal might be an improved chemotherapeutic agent against a retrovirally-induced disease such as AIDS. The following disclosure describes a relatively small group of such compounds.

BRIEF SUMMARY OF THE INVENTION

The present invention contemplates a substituted adenine bonded beta9,1' to a furanosidyl ring having a structure that corresponds to the formula

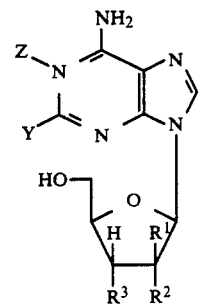

wherein
Z is O— or absent;
Y is halo, $C_1$-$C_6$ lower alkyl or H;
$R^1$ is H, halo or OH;
$R^2$ is H or halo; and
$R^3$ is H, halo, azido or cyano;
with the provisos that:
(a) $R^1=R^2=R^3$ only when $R^1$ is H;
(b) only one of $R^1$, $R^2$ and $R^3$ is halo, azido, or cyano;
(c) $R^1$ is H when $R^2$ is halo;
(d) $R^1$ is H or OH when $R^3$ is halo, azido, or cyano;
(e) Y is H only when Z is O—; and
(f) Y is other than fluoro when (i) Z is absent and (ii) $R^1=R^2=R^3$.

In one preferred embodiment, the Z is absent and the compound has a structure that corresponds to the formula

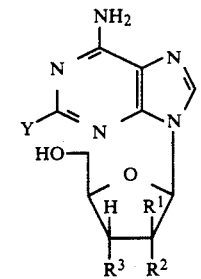

wherein
Y is halo, or $C_1$-$C_6$ lower alkyl;
$R^1$ is H, halo or OH;
$R^2$ is H or halo; and
$R^3$ is H, halo, azido or cyano;
with the provisos that:
(a) $R^1=R^2=R^3$ only when $R^1$ is H;
(b) only one of $R^1$, $R^2$ and $R^3$ is halo, azido or cyano;
(c) $R^1$ is H when $R^2$ is halo;
(d) $R^1$ is H or OH when $R^3$ is halo, azido or cyano; and
(e) Y is other than fluoro when $R^1=R^2=R^3$.

In another preferred embodiment, Z is present (O—) and the compound corresponds to the formula

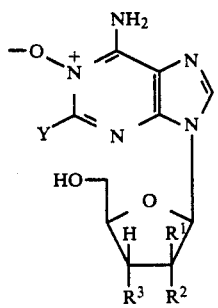

wherein
  Y is halo, $C_1$–$C_6$ lower alkyl or H;
  $R^1$ is H, halo or OH;
  $R^2$ is H or halo; and
  $R^3$ is H, halo, azido or cyano;
with the provisos that:
  (a) $R^1=R^2=R^3$ only when $R^1$ is H;
  (b) only one of $R^1$, $R^2$ and $R^3$ is halo, azido or cyano;
  (c) $R^1$ is H when $R^2$ is halo; and
  (d) $R^1$ is H or OH when $R^3$ is halo, azido or cyano.

Particularly preferred individual compounds include 2-chloro-2',3'-dideoxyadenosine; 2-bromo-2',3'-dideoxyadenosine; 2-methyl-2',3'-dideoxyadenosine; 2',3'-dideoxyadenosine-1-oxide; 2-fluoro-2',3'-dideoxyadenosine-1-oxide; 2-chloro- 2',3'-dideoxyadenosine-1-oxide; and 2-bromo-2',3'-dideoxyadenosine-1-oxide.

Still another aspect of the invention contemplates a method of inhibiting replication of a reverse transcriptase-dependent virus that comprises contacting retrovirus-infected cells with an aqueous composition of a pharmacologically acceptable carrier containing a reverse transcriptase-dependent virus inhibiting but non-toxic amount of a substituted adenine bonded beta-9,1' to a furanosidyl ring that has a structure that corresponds to the formula

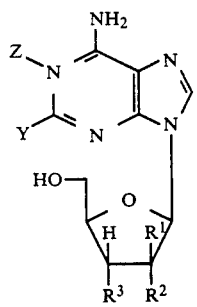

wherein
  Z is O— or absent;
  Y is halo, $C_1$–$C_6$ lower alkyl or H;
  $R^1$ is H, halo or OH;
  $R^2$ is H or halo; and
  $R^3$ is H, halo, azido or cyano;
with the provisos that:
  (a) $R^1=R^2=R^3$ only when $R^1$ is H;
  (b) only one of $R^1$, $R^2$ and $R^3$ is halo, azido or cyano;
  (c) $R^1$ is H when $R^2$ is halo;
  (d) $R^1$ is H or OH when $R^3$ is halo, azido or cyano; and
  (e) Y is H only when Z is O—.

The before-mentioned composition, as well as those aqueous compositions utilized in the method aspects of the invention, can include an effective amount of one or a mixture of the adenine derivatives of the above formulas. Such a composition can also include an effective amount of a second anti-retroviral drug such as AZT and/or 2',3'-dideoxycytidine.

The substituted adenosines described previously all included an adenine bonded 9,1'-beta to the furanosidyl ring. Yet another aspect of the invention contemplates the anomers of those same adenines bonded 9,1'-alpha to a furanosidyl ring, and preferably to a 2',3'-dideoxyribose. Such preferred compounds have a structure that corresponds to the formula

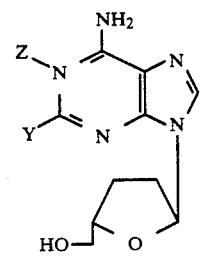

wherein
  Z is O— absent; an
  Y is halo, $C_1$–$C_6$ lower alkyl or H;
with the proviso that Y is H only when Z is present.

Particularly preferred compounds include alpha-2-fluoro-2',3'-dideoxyadenosine; alpha-2-chloro-2',3'-dideoxyadenosine; alpha-2-bromo-2',3'-dideoxyadenosine; alpha-2-methyl-2',3'-dideoxyadenosine, and the 1-N-oxides of each of those compounds, as well as alpha-2',3'-dideoxyadenosine-1-N-oxide.

One of the before-mentioned alpha-anomers as well as alpha-2',3'-dideoxyadenosine can also be utilized in place of or along with one or more of the before-mentioned beta anomers or a compound such as AZT or 2',3'-dideoxycytidine in the before-described method of inhibiting retroviral replication.

Another aspect of the present invention constitutes a composition suitable for inhibiting replication of a retrovirus that comprises a pharmacologically acceptable carrier containing a non-toxic amount of a before-described alpha- or beta-adenosine derivative present in an amount effective to inhibit replication of a reverse transcriptase-dependent virus in cells infected with a retrovirus.

The present invention has several benefits and advantages.

One benefit is that it provides an adenine derivative that can inhibit the replication of a reverse transcriptase-dependent virus in resting, non-stimulated T cells.

One advantage of the invention is that a useful adenine derivative can be utilized at a concentration at which it is relatively non-toxic to the retrovirally-infected cells and other cells of an infected host, but is still effective to inhibit retroviral replication.

Another benefit of the present invention is that the adenine derivative does not substantially inhibit the activity of DNA polymerase-alpha.

Still another benefit of the invention is that the adenine derivative can traverse the membrane of a T lymphocyte and be phosphorylated.

Another advantage of the present invention is that the adenine derivative is substantially free from deamination by adenosine deaminase.

9

Still further benefits of the invention will be apparent to those skilled in the art from the description that follows.

BRIEF DESCRIPTION OF THE DRAWINGS

In the drawings forming a portion of this description:

FIG. 1A shows the cells free of viral infection. FIG. 1B shows the cells infected with HIV but in the absence of added nucleoside. FIGS. 1C, 1D and 1E show the cells infected with HIV, but cultured in the presence of 10 micromolar (uM) amounts of 2-fluoro-2',3'-dideoxyadenosine, 2-chloro-2',3'-dideoxyadenosine and 2-bromo-2',3'-dideoxyadenosine, respectively. The cells were incubated for a period of four days at 37 degrees C.

Figures 1, 2A:
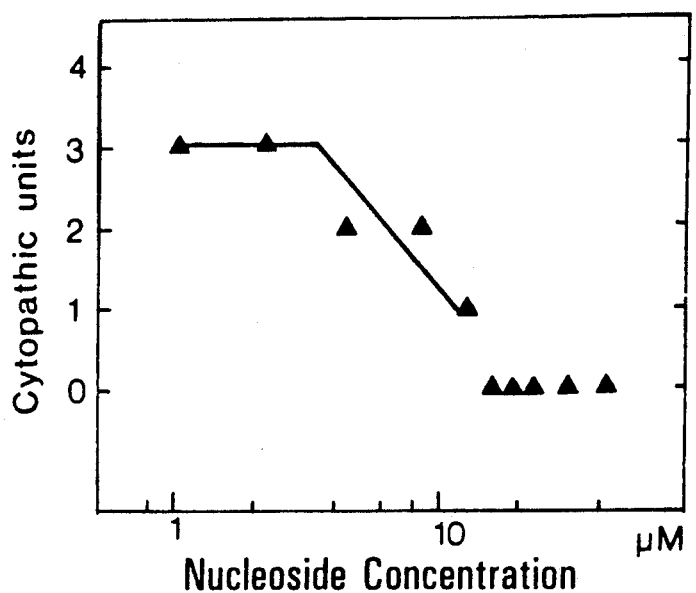
FIGS. 1A-1E contain a series of photomicrographs of cultured MT-2 lymphoblasts-shown at a magnification of 250-fold.
Figures 1, 2B:
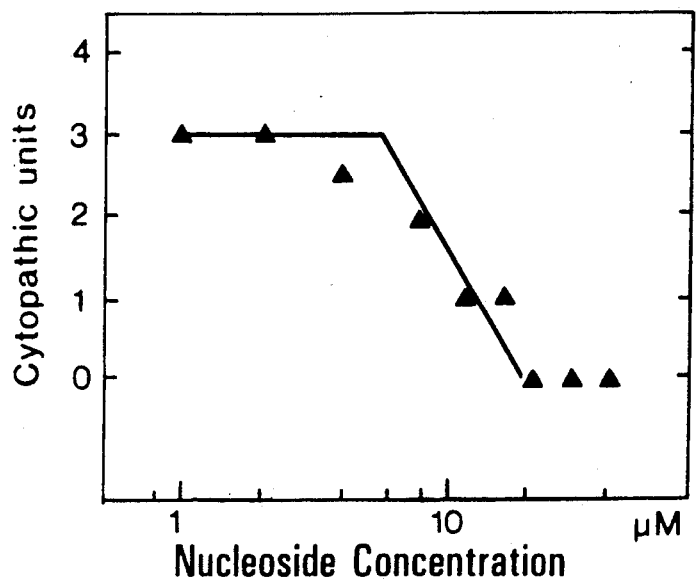
Figures 1, 2C:
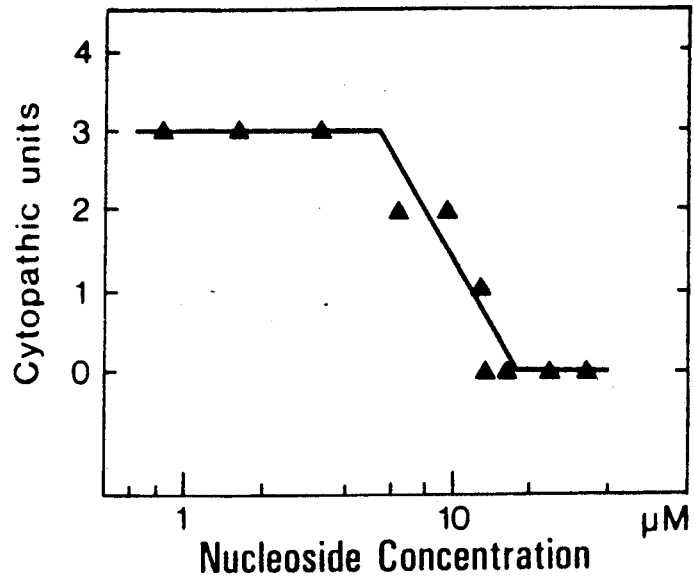
Figures 2, 2A:
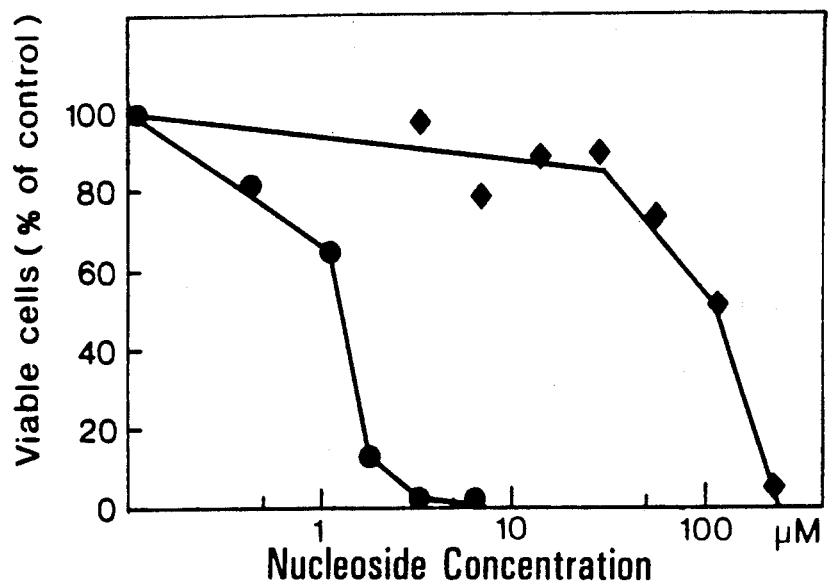
Figures 2, 2B:
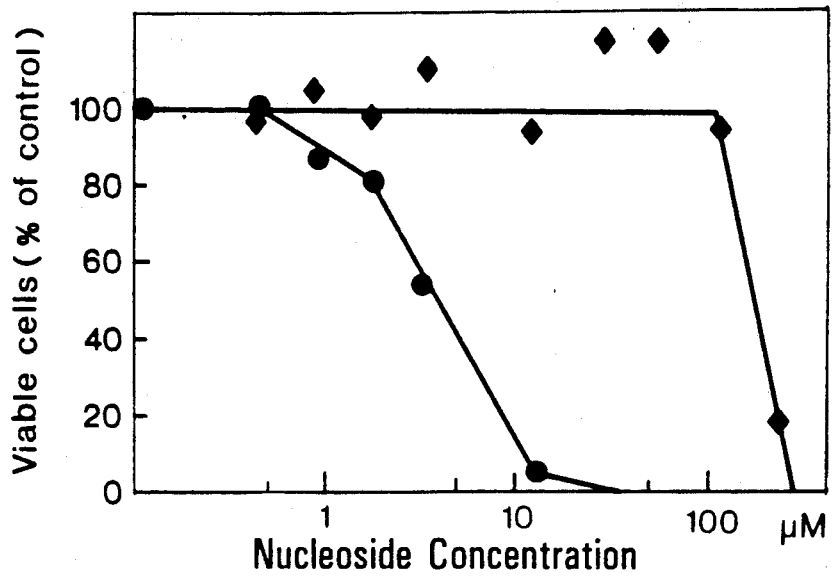
Figures 2, 2C:
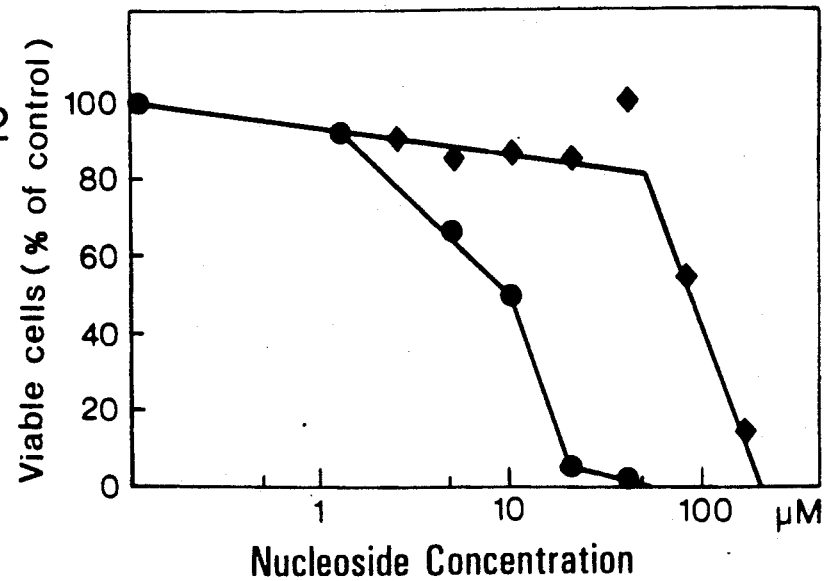

The three graphs in FIGS. 2A-1 through 2C-1 illustrate the inhibition of cytopathic effect of HIV on MT-2 cells by 2-fluoro-2',3'-dideoxyadenosine FIG. 2A-1, 2-chloro-2',3-dideoxyadenosine FIG. 2B-1 and by 2-bromo-2',3'-dideoxyadenosine FIG. 2C-1 at various concentrations of the nucleosides. Cell incubations were carried out for four days at 37 degrees C.

The three graphs in FIGS. 2A-2 through 2C-2 illustrate the growth pattern of CCRF-CEM lymphocytes (closed circles), and a deoxycytidine kinase-deficient mutant (closed diamonds), as measured by the erythrosin B dye method after a time period of 72 hours, and as a function of concentration of the nucleosides of FIGS. 2A-1, 2B-2 2C-1, above, but in the absence of HIV.

Figure 3:
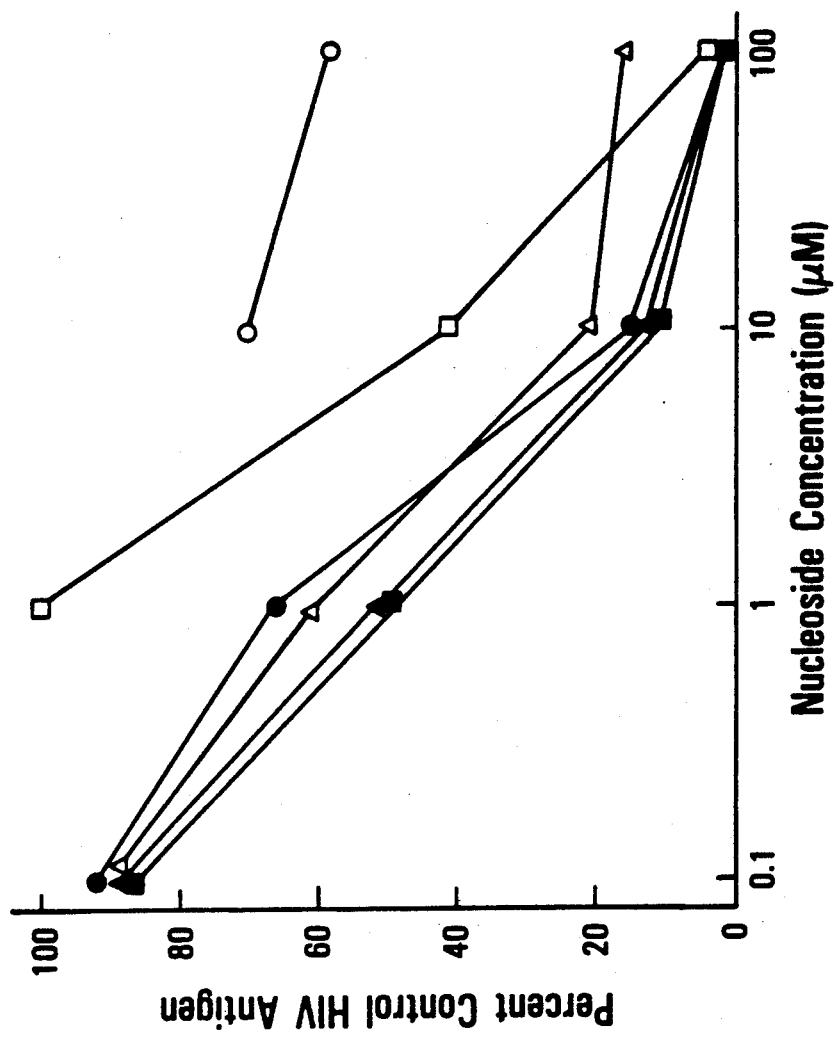

FIG. 3 is a graph that illustrates the anti-HIV effects of 2-chloro-2',3'-dideoxyadenosine (closed circles), 2-bromo-2',3'-dideoxyadenosine (closed squares), and 2',3'-dideoxyadenosine (closed triangles) toward CEM T lymphocytes, as a function of nucleoside concentration, measured by the synthesis of the HIV p 24 (gag) protein after five days. Open symbols show the effects of the respective same dideoxynuceolosides on HIV replication in a deoxycytidine kinase-deficient CEM variant.

DETAILED DESCRIPTION OF THE INVENTION

The present invention contemplates compounds, compositions and methods of use for those compounds and compositions in inhibiting the replication of reverse transcriptase-dependent viruses (RTDVs). Exemplary RTDVs have been noted before and include retroviruses such as HTLV, HIV, FeLV, Mo-MuLV, plant viruses such as cauliflower mosaic virus, and other animal viruses such as hepatitis B virus (HBV).

All of the RTDVs, whether strictly classified as retroviruses such as HIV and Mo-MuLV or not, such as HBV, are often referred to herein for convenience of expression as retroviruses because of their dependence on reverse transcriptase. Similarly, the compounds discussed immediately below are often referred to as anti-retroviral agents or compounds, or the like. The compositions containing those compounds and the method of use of the compounds are also discussed using the word "retrovirus" or a derivative thereof. It is reiterated that the characterization of the target RTDVs as retroviruses is for convenience of expression and is not intended as excluding viruses such as HBV and cauliflower mosaic virus that are also dependent on reverse transcriptase.

10

A. The Compounds

The anti-retroviral compounds of the present invention are substituted adenines that are bonded beta-9,1' to a furanosidyl ring. These compounds have structures that correspond to the general formula

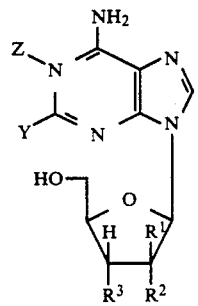

wherein
Z is O— or absent;
Y is halo, $C_1$–$C_6$ lower alkyl or H;
$R^1$ is H, halo or OH;
$R^2$ is H or halo; and
$R^3$ is H, halo, azido, or cyano;
with the provisos that:
(a) $R^1=R^2=R^3$ only when $R^1$ is H;
(b) only one of $R^1$, $R^2$, and $R^3$ is halo, azido or cyano;
(c) $R^1$ is H when $R^2$ is halo;
(d) $R^1$ is H or OH when $R^3$ is halo, azido or cyano;
(e) Y is H only when Z is O—; and
(f) Y is other than fluoro when: (i) Z is absent and (ii) $R^1=R^2=R^3$.

For the above compounds and those described more specifically hereinafter, one group of preferred compounds contains a Y group that is a $C_1$–$C_6$ lower alkyl such as methyl, ethyl, propyl, iso-propyl, butyl, sec-butyl, pentyl and hexyl, of which methyl is more preferred.

In the above formula, and in all other formulas shown herein, hydrogen atoms on the purine and furanosidyl rings that are not needed to show conformation about a particular bond are not shown. Thus, the 7-position purine hydrogen is not shown, nor are the 1'- and 4'-position hydrogens, both of which are in the alpha configuration of the furanoside, nor are the two hydrogens of the 5'-hydroxymethyl group. The hydrogens that indicate beta- or alpha-anomers are also omitted, but a desired anomer can be understood from the text as well as from the depicted furanosidyl ring being drawn in the more usual manner with the 5'-hydroxyl up for the beta-anomer and down for the alpha-anomer.

It is also to be understood that the D isomers of compounds of the formulas are the isomers contemplated. It is further to be noted that the designation "halo" used hereinafter is meant to include fluorine, chlorine and bromine derivatives, and to exclude iodine derivatives, which are unstable and decompose, and astatine derivatives that are radioactive. Where specific halogen derivatives are intended, those compounds are named specifically.

In all of the compounds of the above formula, it is preferred that $R^1=R^2=R^3=H$.

In some preferred embodiments, the Z group, O—, is absent and Y is as above; i.e., other than fluorine. The Z group is present in other embodiments and Y is hydrogen (H) in some. In still other embodiments, Z is present and Y is present, as described before, and in that embodiment, Y is preferably halo or methyl.

Thus, a compound of the embodiment where Z is absent constitutes a substituted adenine bonded beta-9,1' to a furanosidyl ring, and has a structure that corresponds to the formula

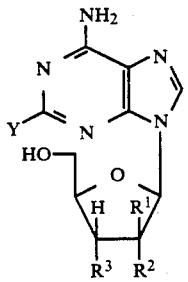

wherein
Y is halo, or $C_1$-$C_6$ lower alkyl;
$R^1$ is H, halo or OH;
$R^2$ is H or halo; and
$R^3$ is H, halo, azido or cyano;
with the provisos that:
(a) $R^1 = R^2 = R^3$ only when $R^1$ is H;
(b) only one of $R^1, R^2$, and $R^3$ is halo, azido or cyano;
(c) $R^1$ is H when $R^2$ is halo;
(d) $R^1$ is H or OH when $R^3$ is halo, azido or cyano; and
(e) Y is other than fluoro when $R^1 = R^2 = R^3$.

Most preferred compounds of this embodiment, are 2-chloro-2',3'-dideoxyadenosine, 2-bromo-2',3'-dideoxyadenosine and 2-methyl-2',3'-dideoxyadenosine, of which the above 2-chloro- and 2-bromo-derivatives are particularly preferred.

Compounds of the embodiments where Z (O—) is present constitute substituted adenine 1-N-oxides bonded beta-9,1' to a furanosidyl ring and have a structure that corresponds to the formula

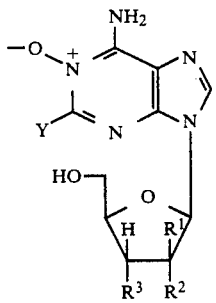

wherein
Y is halo, $C_1$-$C_6$ lower alkyl or H;
$R^1$ is H, halo or OH;
$R^2$ is H or halo; and
$R^3$ is H, halo, azido or cyano;
with the provisos that:
(a) $R^1 = R^2 = R^3$ only when $R^1$ is H;
(b) only one of $R^1, R^2$, and $R^3$ is halo, azido or cyano;
(c) $R^1$ is H when $R^2$ is halo; and
(d) $R^1$ is H or OH when $R^3$ is halo, azido or cyano.

A group of particularly preferred compounds contains a Y group that is a halo substituent. Specific, most preferred compounds of this group include 2-fluoro-2',3'-dideoxyadenosine-1-oxide, 2-chloro-2',3'-dideoxyadenosine-1-oxide and 2-bromo-2',3'-dideoxyadenosine-1-oxide.

In another group of compounds whose structures correspond to the above formula, Y is H. Here, a most preferred specific compound is 2',3'-dideoxyadenosine-1-oxide.

The adenosine-1-N-oxide group of compounds are of particular interest since those materials, per se, are most likely not incorporated into a growing polynucleotide chain since the presence of the N-oxide group probably interferes with hydrogen bonding during that synthesis. Rather, it is believed that the N-oxide compounds are reduced by an endogenous reductase prior to their incorporation into and termination of the growing chain.

Nevertheless, being free from a net ionic charge, but possessing an internal zwitterionic charge pair, the N-oxide compounds can penetrate T cell membranes. Those compounds are also somewhat more water-soluble than are the corresponding un-oxidized compounds.

Without wishing to be bound by theory, it is nevertheless believed that the N-oxide compounds enter the cell and are phosphorylated, in keeping phosphorylation in Lindberg et al. (1967) *J. Biol. Chem.*, 242:350–356. A pool of such derivatives is maintained intracellularly until such time as the N-oxide function is reduced and the nucleotide is incorporated to terminate the appropriate, growing polynucleotide chain.

It is not known what reductase enzyme operates here, nor whether it operates on a mono-, di-, or tri-phosphate, or whether it acts on the unphosphorylated compound. Inasmuch as the N-oxides are substrates for the kinase enzymes, it would appear as though the reductase probably acts upon a phosphorylated molecule. Regardless of which form of an N-oxide is reduced, use of an N-oxide derivative even for 2',3'-dideoxyadenosine-1-N-oxide avoids the problem of the relatively high level of adenosine deaminase found in the blood of AIDS patients.

Additional, specific, useful compounds corresponding to one of the before-mentioned formulas are shown in Table 1, below, wherein Z, Y, $R^1$, $R^2$, $R^3$ and $R^4$ are as before described.

TABLE 1

| | Further Useful Compounds[a] | | | | |
|---|---|---|---|---|---|
| Compound Number | $Z^b$ | $Y^c$ | $R^1$ | $R^2$ | $R^3$ |
| 1 | O— | Cl | OH | H | H |
| 2 | O— | Br | H | H | Br |
| 3 | O— | $CH_3$ | H | H | $N_3$ |
| 4 | O— | i-$C_3H_7$ | H | H | H |
| 5 | O— | $C_5H_{11}$ | H | Cl | H |
| 6 | O— | F | F | H | H |
| 7 | O— | Cl | H | H | Br |
| 8 | O— | $C_2H_5$ | H | H | H |
| 9 | O— | H | H | H | H |
| 10 | O— | $CH_3$ | F | H | H |
| 11 | O— | H | OH | H | CN |
| 12 | O— | H | H | H | $N_3$ |
| 13 | O— | H | H | H | Cl |
| 14 | Abs. | s-$C_4H_9$ | H | H | H |
| 15 | Abs. | Cl | OH | H | H |
| 16 | Abs. | Br | H | Cl | H |
| 17 | Abs. | $C_6H_{13}$ | H | H | OH |
| 18 | Abs. | F | F | H | H |
| 19 | Abs. | Cl | Cl | H | H |
| 20 | Abs. | Br | F | H | H |
| 21 | Abs. | $CH_3$ | F | H | H |
| 22 | Abs. | Cl | H | H | CN |
| 23 | Abs. | F | H | H | $N_3$ |
| 24 | Abs. | $CH_3$ | OH | H | $N_3$ |
| 25 | Abs. | $C_3H_7$ | H | H | CN |
| 26 | Abs. | Cl | OH | H | CN |

TABLE 1-continued

Further Useful Compounds[a]

| Compound Number | Z[b] | Y[c] | R[1] | R[2] | R[3] |
|---|---|---|---|---|---|
| 27 | Abs. | Cl | H | Br | H |

[a]Valence bonds for substituents are not shown in the Table.
[b]The designation "O—" indicates that Z is present as the N—oxide, whereas the designation "Abs." indicates that Z is absent.
[c]The designation "i-" and "s-" indicate "iso" and "secondary" alkyl configurations, respectively.

The compounds of the above Table can be named as follows: (1) 2-chloro-9,1'-beta-3'-deoxy-D-arabinofuranosyladenine-1-oxide; (2) 2-bromo-9,1'-beta-2',3'-dideoxy3'-azido -D-ribofunarosyladenine-1-oxide; (4) 2-(iso-propyl)-9,1'-beta-2',3'-dideoxy-3'-azido-D-ribofuranosyladenine-1-oxide; (5) 2-pentyl-9,1'-beta-2',3'-dideoxy-2'-chloro-D-ribofuranosyladenine-1-oxide; (6) 2-fluoro-9,1'-beta- 2',3'-dideoxy-2'-fluoro-D-arabinofuranosyladenine-1-oxide; (7) 2-chloro-9,1'-beta-2',3'-dideoxy-3'-bromo-D-ribofuranosyladenine-1-oxide; (8) 2-ethyl-9,1'-beta-2',3'-dideoxy-3'-fluoro-D-ribofuranosyladenine-1-oxide; (9) 9,1'-beta-2',3'-dideoxy-3'-azido-D-ribofuranosyladenine-1-oxide; (10) 2-methyl-9,1'-beta-2',3'-dideoxy-2'-fluoro-D-arabinofuranoyladenine-1-oxide; (11) 9,1'-beta-3'-deoxy-3'-cyano-D-arabinofuranosyladenine-1-oxide; (12) 9,1'-beta-2',3'-dideoxy-3'-azido-D-ribofuranosyladenine-1-oxide; (13) 9,1'-beta-2',3'-dideoxy-3'-chloro-D-ribofuranosyladenine-1-oxide; (14) 2-(sec-butyl)-9,1'-beta-2',3'-dideoxy-D-ribofurano syladenine; (15) 2-chloro-9,1'-beta-3'-deoxy-D-arabinofuranosyladenine; (16) 2-bromo-9,1'-beta-2',3'-dideoxy-2'-chloro-D-ribofuranosyladenine; (17) 2-hexyl-9,1'-beta-2',3'-dideoxy-3'-azido-Dribofuranosyladenine; (18) 2-fluoro-9,1'-beta-2',3'-didexoy-2'-fluoroarabinofuranosyladenine; (19) 2-chloro-9,1'-beta-2'-3'-dideoxy-2'-fluoro-D-arabinofuranosyladenine; (20) 2-bromo-9,1'-beta-2',3'-dideoxy-2'-chloro-D-arabinofuranosyladenine; (21) 2-methyl-9,1'-beta-2',3'-dideoxy-2'-fluoro-D-arabinofuranosyladenine; (22) 2-chloro-9,1'-beta-2',3'-dideoxy-3'-cyano-D-ribofuranosyladenine; (23) 2-fluoro-9,1'-beta-2',3'-dideoxy-3'-azido-D-ribofuranosyladenine; (24) 2-methyl-9,1'-beta-3'-deoxy-3'-azido-D-arabinofuranosyladenine; (25) 2-propyl-9,1'-beta-2',3'-dideoxy-3'-cyano-D-ribofuranosyladenine; (26) 2-chloro-9,1'-beta-3'-deoxy-3'-cyano-Darabinofuranosyladenine; and (27) 2-chloro-9,1'-beta-2'-bromo-2',3'-dideoxy-D-ribofuranosyladenine.

As will be noted from some of the before-recited provisos, 2-fluoro-2',3'-dideoxyadenosine is specifically excluded. This compound has been previously reported in the literature. See for example, U.S. Pat. No. 3,817,982. 2-Fluoro-2',3'-dideoxyadenosine is thus excluded by the proviso that Y is other than F (fluoride) when $R^1 = R^2 = R^3$, since another proviso limits the R groups to being the same only where one of them is hydrogen (H). Although not new, the above compound is useful in a method of this invention, as discussed hereinafter.

A compound of the invention is typically contacted with retrovirally-infected cells in an aqueous medium of a pharmacologically acceptable carrier via intravenous infusion. That method of contacting, while effective, is inconvenient and time consuming.

Oral administration of a solid form of the compound (in which case the ultimate carrier is a body fluid such as stomach or intestinal fluid, serum or lymph even though a carrier described hereinafter can be utilized for the initial administration) of the recipient containing the dissolved compound, or an administration of an aqueous preparation designed for oral administration as is hereinafter discussed is a particularly attractive mode of administration. One draw back of oral administrations of such compounds, however, is their potential decomposition in the acidic conditions of the stomach. That is, the glycosidic bond tends to hydrolyze under acid conditions, and 2',3'-dideoxyadenosine reportedly undergoes such a hydrolysis about 40,000 times faster than does adenosine itself [York (1981) *J. Org. Chem.*, 46:2171-2173].

Thus, where oral administration is desired, substitutions on the adenine ring of the before-mentioned preferred and particularly preferred compounds are utilized along with a 2'-halo-substituted arabinofuranosidyl ring. Of the 2'-halo derivatives, a flourine atom is particularly preferred. Compounds 6, 10 and 18-21 of Table 1, above, exemplify these compounds.

Marquez et al. (1987) *Biochem. Pharm.*, 36:2719-2722 reported preparation of 2'-fluoro-2',3'-dideoxyribose and 2'-fluoro-2',3'-dideoxyarabinose derivatives of adenine. Their findings stated that both derivatives were stable at a pH value of 1 at 37 degrees C., whereas dideoxyadenosine had a half time of 35 seconds under those conditions. They reported that the ribosyl derivative was more toxic than the arabinosyl derivative. They further reported that the arabinosyl derivative was about as active and as potent as AZT or dideoxyadenosine in protecting ATH8 cells in vitro against the cytopathic effect of HIV under conditions of substantial viral excess.

Each of the previously-discussed compounds is phosphorylated by T cells, and preferably by resting, non-stimulated cells, as compared to stimulated T cells. The principal enzyme or enzymes that carry out that phosphorylation are believed to be adenosine kinase and/or deoxycytidine kinase. One or more additional enzymes may also play a role in that phosphorylation.

Each of the previously discussed compounds is also substantially free of deamination by adenine deaminase (calf intestinal adenosine deaminase being used as a typical adenosine deaminase). Exemplary data for the 2-halo-2',3'-dideoxyadenosine (2-halo-ddA) derivatives are shown hereinafter. Those data, as well as the data published by Coddington (1965) *Biochim. Biophys. Acta*, 99:442-451 and others discussed before indicate that the abilitiy of an adenine derivative to be or not to be a substrate for adenosine deaminase is more a function of the substitution or lack of substitution on the adenine portion of the molecule than a function of substituents on the linked sugar ring portion, at least as far as the substituents on both rings herein are concerned.

It is believed that the compounds useful herein act to inhibit viral replication by terminating an otherwise growing polynucleotide chain. More specifically, it is thought that the intracellular 5'-triphosphates formed from those compounds are utilized by the retroviral reverse transcriptase or another polynucleotide synthetase such as one of the before-discussed DNA polymerases to terminate a growing polynucleotide chain and thereby inhibit growth (replication) of the retrovirus.

For example, Chidgeavedze et al. (1985) *FEBS Lett.*, 183:275-278 reported that 3'-fluoro-2',3'-dideoxyadenosine, guanosine, cytidine and thymidine were substrates for *E. coli* DNA polymerase I, ovian myeloblastosis virus reverse transcriptase and Bollum terminal deoxyribonucleotidyl transferase, and acted as chain terminators for each enzyme. Similarly, Schroeder et al. (1980) *Z. Allg. Mikrobiol.* 20 657–662 reported 3'-fluorothymidine 5'-triphosphate (the triphosphate of the above 3'-fluorothymidine compound) to inhibit DNA synthesis by T4 wild-type, L98 (mutator) and CB121 (antimutator) DNA polymerases.

Regardless of the mechanism, and enzyme or enzymes at which the compound acts, replication of the virus is inhibited. Such inhibition of retroviral replication can be readily ascertained, whereas the mechanism of action and the enzyme or enzymes involved in that inhibition of replication are more difficult to ascertain.

A compound useful in the present invention can be prepared by a number of well known routes. The chemistry involved in such syntheses is not deemed to be a part of this invention other than by the production of useful compounds.

Exemplary syntheses for the 2-halo-2',3'-dideoxyadenosines and adenosine-1-N-oxide are provided hereinafter, and are carried out by the method of Klenow et al. (1961) *Biochim. Biophys. Acta,* 52:386–389, with slight modifications. In addition, it is noted that the N-oxide derivatives can be prepared from the corresponding un-oxidized compounds by the synthetic route described, so nothing further need be said about those compounds.

The starting materials for the respective syntheses are the 2-substituted derivatives of adenine. Each of the useful compounds can be generated by enzymatic transglycosylation to the appropriate adenine, using crude bacterial enzyme sources.

Both 2-chloroadenine and 2-bromoadenine have been prepared by treatment of the commercially available 2,6-dichloropurine and 2,6-dibromopurine with dry methanolic ammonia [Brown et al. (1958) *J. Org Chem.,* 23:125–127]. Several grams of 2-fluoroadenine, prepared from 2,6-diaminopurine by the modified Schiemann reaction [Montgomery et al. (1960) *J. Am. Chem. Soc.,* 82:463–468], have been kindly supplied by Dr. John Montgomery (Southern Research Institute). 2-Methyladenine is available commercially from Sigma Chemical of St. Louis, MO. The other 2-alkyladenines can be prepared by well known methods.

The 2-substituted-2'-deoxynucleosides are made by transfer of the deoxyribose moiety from thymidine to the respective adenine base, catalyzed by a partially purified trans-deoxyribosylase from *Lactobacillus helveticus* (ATCC 8018) [Carson et al. (1980) *Proc. Natl. Acad. Sci. USA,* 77:6865–6869 and McGarrity et al. (1982) *Exp. Cell Res.,* 139:199–295]. In a typical synthesis, the purine base (about 5 mg/ml) is suspended in 10 mM potassium phosphate at pH 5.9 and then is mixed vigorously with a two-fold molar excess of thymidine and with 1 mg/ml of crude Lactobacillus helveticus enzyme.

The reaction is maintained at room temperature, and is monitored by thin layer chromatography (TLC). The purine deoxynucleoside is more soluble than the base, and the solution becomes less cloudy as the reaction proceeds. After an incubation for about eighteen hours (overnight) the reaction mixture is brought to pH 12 by the addition of NH4OH and is applied to AG1X-8 resin (formate form, one liter per 5–10 g nucleoside), packed in a scintered glass funnel connected to a vacuum flask. After removal of protein with 10 mM NH4OH, the product is eluted with 20 percent methanol in NH4OH and dried. Purity is confirmed by HPLC and NMR. The method has been used to prepare 10 g quantities of 2-chloro-2'-deoxyadenosine, and 2–5 g quantities of 2-fluoro-2'-deoxyadenosine and 2-bromo-2'-deoxyadenosine.

The preparation of 3'-substituted derivatives of 2-substituted-2'-deoxyadenosine typically starts with the 2-substituted- 2'-deoxynucleosides, whose 5'-hydroxyl groups are protected with tert-butyldimethylsilyl chloride in pyridine. Formation of the 3'-O-triflate (or the 3'-O-mesylate) followed by nucleophilic displacement yields various 2'-deoxy-3'-substituted compounds in the xylo form. Substitution of the 3'-xylo derivative by another nucleophile, e.g., halide, azide or cyanide, provides a further inversion at the 3'-position to provide a desired compound. For example, reaction of the 2'-deoxyribosyl-3'-O-triflate (or 3'-O-mesylate) with NaOAc, followed by deacetylation, (or with NaOH instead of NaOAc) can generate the relevant 5'-protected-2'-deoxynucleoside with an inverted 3'-hydroxyl group (the xylo form). Subsequent 3'-O-triflation (or 3'-O-mesylation), nucleophilic displacement, and deprotection of the 5'-protected nucleoside yields the 3'-substituted derivative in the down position, ribo form.

The 2',3'-dideoxynucelosides can be prepared from the corresponding 2-deoxynucleosides in four steps. In this procedure, the 2-substituted-5'-protected-2'-deoxynucleosides are reduced to the corresponding 2',3'-dideoxynucleosides utilizing the initiated Barton reduction described in Robins et al. (1983) *J. Am. Chem. Soc.,* 105:4059–4065 for the conversion of purine ribonucleosides to 2'-deoxyribonucleosides.

The preparation of 2-chloro-2',3'-dideoxyadenosine is exemplary. First, the 5'-hydroxyl group of the 2-substituted-2'-deoxyadenosine is protected by reaction with 4,4'-dimethoxytrityl chloride in pyridine. The 2-substituted-5'-dimethoxytrityl-2'-deoxyribonucleoside is reacted for 16 hours at room temperature with phenyl chlorothionocarbonate in fresh acetonitrile, using 4-dimethylaminopyridine as catalyst. After evaporation of the acetonitrile, the 5'-dimethoxytrityl group is removed from the 2-substituted-3'-phenoxythiocarbonyl derivative with 80 percent acetic acid. The resulting 3'-phenoxythiocarbonyl-2'-deoxynucleoside is dried, and suspended in toluene containing 2,2'-azobis(2-methylpropionitrile). After purging with nitrogen, and the addition of 1.5 equivalents tri-n-butylin hydride, the reaction mixture is maintained at 75 degrees C. for 6 hours. The resultant 2-substituted-2',3'-deoxynucleoside is purified by preparative TLC on silica gel plates using 10 percent methanol in chloroform.

Compounds containing 2'- and 3'-substituents and the 2'-substituted-3'-deoxy compounds are also prepared via the desired 2-substituted adenine. For these compounds, appropriately substituted adenosines and arabinoadenosines (ara-A) are formed from the adenines in another enzyma ic trans-glycosylation procedure.

No enzyme exists for the direct transfer of the ribose or arabinose moieties of purine and pyrimidine nucleosides. However, Utagawa et al. U.S. Pat. No. 4,371,613 and Krenitsky et al. (1981) *Biochem.,* 20:3615-3621 (whose disclosures are incorporated by reference) reported that bacterial phosphatases were destroyed by heat treatment at 60–65 degrees C., whereas the purine and pyrimidine nucleoside phosphorylases remained fully active. Hence, one can use a heat-treated bacterial (*E. coli*) extract for both trans-ribosylation and transarabinosylation. A heat treated *E. coli* extract has been successfully used for the preparation of 2-fluoroadenosine and 2-fluoro-ara-A starting with 2-fluoroadenine and a bacterial extract is discussed hereinafter. The same method is applicable to the 2-substituted derivatives.

To prepare the E. coli enzyme, 150 gm of lyophilized cells (available commercially from Sigma) were suspended in 0.1 M $KH_2PO_4$, pH 6.0, and were disrupted in a Servall grinder. Cell debris was removed by centrifugation at 7000 rpm for one hour. Proteins precipitating between 30-65 percent saturated ammonium sulfate were isolated, dialyzed against water, and heated for 4 hours at 61 degrees C. After removal of precipitates, the enzyme was aliquoted and stored at −20 degrees C.

In an exemplary synthesis to form 2-fluoro-ara-A (or 2-fluoro-adenosine), uracil beta-D-arabinofuranoside (or uridine), and 2-fluoroadenine were suspended in 30 mM $KH_2PO_4$ pH 7.0, containing 5 mg/ml of E. coli extract, and the mixture was stirred for 6-24 hours at 60 degrees C. The pyrimidine bases should be present in at least two-fold molar excess, compared to 2-fluoroadenine. The reaction was monitored by HPLC, and was terminated by the addition of an equal volume of ethanol. After removal of precipitated bacterial protein, the nucleosides were fractionated by chromotography on AG1X-8, as described before. In some cases, it was necessary to repeat the chromatography to obtain a clean product.

Fukukawa et al. (1980) *Chem. Pharm. Bull.*, 31:1582–1592 recently described a simple, four-step procedure for the generation of 2'-substituted adenosine derivatives. That method has been used to prepare 2'-ara-chloro and 2'-ara-azido derivatives of 2'-deoxyadenosine and 2-chloro-2'-deoxyadenosine, one of whose starting adenosines was prepared by the above trans-glycosylation procedure.

In a representative synthesis, a 2-substituted-adenosine or 2-substituted-ara-A derivative in dry pyridine is added to 1,1,3,3-tetraisopropyl disiloxane dichloride at zero degrees C., in order to protect the 3'- and 5'-hydroxyl groups. After stirring at room temperature for 1-3 hours, pyridine is evaporated, and the residue is partitioned between ethyl acetate and aqueous NaCl. The organic phase is washed with cold 0.5 N HCl, and dried.

To generate the 2'-O-triflate or -mesylate, the 3',5'-protected nucleoside, and a small amount of 4-dimethylaminopyridine, are dissolved in methylene chloride, and the solution is treated with trifluoromethane sulfonyl chloride or methane sulfonyl chloride at room temperature. The reaction is monitored by TLC. The 2'-O-triflate or 2'-O-mesylate is recovered by preparative TLC, and dissolved in hexamethylphosphoric triamide. A nucleophile, such as LiCl, LiF or NaOAC, is added to the solution, to generate the 2'-substituted derivative, which is then recovered from the reaction mixture by preparative TLC.

Deprotection is effected by dissolving the 2'-substituted derivative at room temperature in a solution of tetra-n-butyl ammonium fluoride in tetrahydrofuran. After the deprotection is complete, the 2'-substituted-2'-deoxynucleoside is purified by preparative TLC, extracted with methanol, concentrated by evaporation and dried. Purity is confirmed by NMR and HPLC analysis.

Depending upon whether or not the reaction is begun with 2-substituted adenosine or 2-substituted-ara-A, one can obtain a series of 2'-derivatives with substitutions in the up (ara) or down (ribo) configuration, utilizing the same reactions. Furthermore, nucleophilic displacement of the 2'-O-triflate or 2'-O-mesylate with NaOAc, followed by deacetylation, or with NaOH offers a practical method for the inversion of the 2'-hydroxyl group.

Once the 2'-substituent is in the desired up (ara) or down (ribo) configuration, the 3'—OH is removed as discussed previously for the preparation of 2-substituted-2',3'-dideoxy compounds from a corresponding 2-substituted-2'-deoxy compound. Thus, the 5'-OH is blocked with a dimethoxytrityl group, and the 3'-hydroxyl is reacted with phenyl chlorothionocarbonate. The dimethoxytrityl group is removed, and after drying, the resultant compound is reacted with 2,2'-azobis(2-methylpropionitrile) and tri-n-butyltin hydride. The resulting compound is thereafter recovered by preparative TLC (PLC) or HPLC or the like.

For 2-substituted adenine derivatives containing an azido, cyano or halo group at the 3'-position, the above synthetic scheme is followed through the formation of the 2'-substituent in the desired up or down configuration, deprotection of 3'- and 5'-OH groups, and reprotection of the 5'—OH with a group such as dimethoxytrityl. The desired 3'-azido, 3'-cyano or 3'-halo derivative is thereafter formed as described for the previously described 3'-substituted-2'-deoxy compounds.

The 3'-deoxy-2'-substituted (or arabino)-adenosine-1-N-oxides are readily prepared from 3'-deoxyadenosine (cordycepin) that is available commercially, e.g., Sigma Chemical Co. of St. Louis, MO. Here, the 5'-hydroxyl is protected as discussed previously, and a 2'-O-triflate or 2'-O-mesylate derivative is formed, as is also described previously. Appropriate nucleophilic substitution at the 2'-position affords the substituted arabino form of the furanoside. Further substitution at that 2'-position can provide a 5'-protected-2',3'-dideoxy-2'-halo-ribofuranoside. The 5'-protecting group is thereafter removed from the arabino or ribo form, and the compound is oxidized to form the corresponding 1-N-oxide, as also discussed before.

The above compounds can, of course, be prepared by numerous other routes. For example, the appropriately substituted adenine can be condensed directly to an appropriately substituted sugar ring as by the techniques described in Montgomery et al., (1986) *J. Med. Chem.*, 29:2389-2392, by the method taught in U.S. Pat. No. 4,082,911, or as described in the citations of note (22) of Herdewijn et al. (1987) *J. Med. Chem.*, 30:2131–2137, which disclosures are incorporated herein by reference. Still further, Wright et al. (1987) *J. Org. Chem.*, 52:4617-4618 recently prepared 2-chloro- and 2-bromo-2'-deoxyadenosines by direct reaction of the appropriate 2,6-dihalo purine with a 3',5'-protected-alpha-1-chlororibose using sodium hydride in acetonitrile, followed by treatment with methanolic ammonia at 60 degrees C. to deprotect the resulting 3',5'-hydroxyls and form the 6-amino group of the finally produced adenosine. This disclosure is also incorporated by reference.

The alpha-anomers of some of the before-discussed beta-adenosine derivatives are also useful herein. Indeed, while being different from the beta anomers, the alpha anomeric compounds share several properties with the beta-anomers.

For example, Yamaguchi et al. (1984) *Chem. Pharm. Bull.*, 32:1441-1450, reported that alpha-deoxyadenosine had affinity for cellular deoxyribonucleoside kinase, albeit a weaker affinity than its beta-counterpart.

Those workers also reported that alpha-dATP exhibited a weak inhibitory effect on alpha- and beta-DNA polymerases.

LePage et al. (1965) *Cancer Res.*, 25:46-52 reported that the alpha-anomers of arabinosyladenine and xylosyladenine were not deaminated by extracts of mouse TA3 or L1210 tumor cell suspensions, whereas their beta-anomers were deaminated. That paper indicates, in addition, that a nucleoside phosphorylase acts upon the alpha-anomers.

Falke et al. (1979) *Biochim. Biophys. Acta*, 563:36-45 reported on studies with herpes simplex virus (HSV) type 1 and type 2 with the beta- and alpha-anomers of arabinoadenosine. Their results indicated that the alpha-anomer did not inhibit muliplication of HSV, although that compound was a strong inhibitor of proliferation of non-infected cells. The alpha-anomer also exhibited no effect on the incorporation of deoxythymidine into HSV DNA, but did block incorporation of that nuceloside into host cell DNA, and was incorporated into newly synthesized host cell DNA but not into HSV DNA. The beta-anomer had an affect on the incorporation of deoxythymidine into both viral and host DNAs.

Montgomery in *Nucleosides, Nucleotides and their Biological Applications,* Rideout et al. eds., "Proceedings of the 5th International Round Table", Oct. 20-22, 1982, Academic Press, New York (1983) pages 19-46, reported inhibition of growth of human epidermoid carcinoma cells in culture using a variety of 2-fluoroadenine and 2-fluoroadenosine derivatives. The reported results indicated that about 5-30 times the amount of the alpha-anomers of 2-fluoroadenosine and 2-fluroarabinoadenosine was required to inhibit cell growth as compared to the beta-anomers.

Somewhat further afield, LePage et al. (1966) *Mol. Pharmacol.*, 3:37-43 reported that the alpha-anomer of 2'-deoxythioguanosine was incorporated into polynucleotide chains of Mecca Lymphosarcoma ascites cells in mice in vivo. The alpha-anomers appeared to be incorporated into both RNA and DNA. In addition, incorporation of the alpha-anomer into DNA resulted in a relatively higher level of terminal incorporation than for the beta-anomer. Thus, the alpha-anomers obviously penetrated the cell membranes in vivo, and were substrates for the appropriate kinase and polymerase enzymes.

The preferred alpha-anomeric adenine derivatives contemplated herein are bonded 9,1'-alpha to a furanosidyl ring, particularly a 2',3'-dideoxyribose ring. Those compounds have a structure that corresponds to the formula

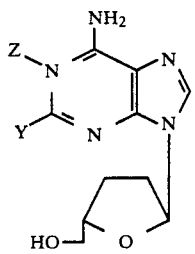

wherein

Z is O— or absent; and

Y is halo, $C_1-C_6$ lower alkyl or H;

with the proviso that Y is H only when Z is present.

Y, Z, $C_1-C_6$ lower alkyl and halo have the same meanings for the alpha-anomers as they did hereinbefore for the beta-anomers. As can be seen from the sole proviso; i.e., that Y is H (hydrogen) only when Z is present, alpha-2',3'-dideoxyadenosine is excluded from the compounds of the formula immediately above.

Particularly preferred alpha-anomers include alpha-2-fluoro-2',3'-dideoxyadenosine; alpha-2-chloro-2',3'-dideoxyadenosine; alpha-2-bromo-2',3'-dideoxyadenosine; alpha-2-methyl-2',3'-dideoxyadenosine; alpha-2-fluoro-2',3'-dideoxyadenosine 1-N-oxide; alpha-2-chloro-2',3'-dideoxyadenosine-1-N-oxide; alpha-2-bromo-2',3'-dideoxyadenosine-1-N-oxide; alpha-2-methyl-2',3'-dideoxyadenosine-1-N-oxide; alpha-2-methyl-2',3'-dideoxyadenosine-1-N-oxide; and alpha-2',3'-dideoxyadenosine-1-N-oxide.

The above alpha-anomers can also be prepared in a number of manners.

One of these methods is that of Yamaguchi et al. (1984) *Chem. Pharm. Bull.,* 32:1441-1450. That method utilizes a non-enzymatic transglycosylation reaction. A 2-substituted adenine (2-SA), protected at the 6-position by a benzoyl group, is admixed in anhydrous acetonitrile with bis-trimethylsilylacetamide (BSA) and 3',5'-di-O-acetyl-4-N-benzoyl-2'-deoxycytidine (dAC-Nb-dC) at a molar equivalent ratio of 9.6 2-SA: 15 BSA:3.6 dAC-Nb-dC. That admixture is heated and stirred at 70 degrees C. to provide a clear solution. Trimethylsilyl t ifluoromethanesulfonate (TMS-triflate) at 4.7 molar equivalents is then added to the clear solution. The resulting admixture is stired for about 4 hours.

Thereafter, the solvent is removed under reduced pressure, and the residue is partitioned between an organic solvent such as chloroform and aqueous sodium bicarbonate. After removing the organic solvent, the residue is separated chromatographically on silica gel.

The anomeric mixture of 3',5'-di-O-acetyl-6-N-benzoyl-2'-deoxyadenosines is treated with methanol saturated with ammonia in a sealed stainless steel vessel at about 40 degrees C. for about 12 hours. After removing the solvent, the residue is dissolved in distilled water and separated on a Dowex 1 chromatography column (hydroxide form) using distilled water as eluant to provide the separated anomers.

Further syntheses of alpha-anomers of 2-substituted-2'-deoxyadensines are reported in Montgomery et al. (1969) *J. Med. Chem.*, 12:498-504; Montgomery et al. (1974) *J. Med. Chem.*, 17:1197-1207; and Wright et al. (1987) *J. Org. Chem.*, 52:4617-4618, whose disclosures are incorporated herein by reference.

The desired alpha-2-substituted-2',3'-dideoxyadenosine can be prepared from the corresponding alpha-2-substituted-2'-deoxyadenosine by the procedure of Robins et al. (1983) *J. Am. Chem. Soc.*, 105:4059-4065 as described before and illustrated hereinafter for the beta-anomers. The 1-N-oxide derivatives are prepared by the oxidation procedure of Klenow et al. (1961) *Biochim. Biophys. Acta,* 52:386-389 discussed before for the beta-anomers, and illustrated hereinafter.

B. The Methods

Another aspect of the present invention is a method of inhibiting replication of a RTDV that comprises contacting retrovirus-infected cells with an aqueous composition of a pharmacologically acceptable carrier containing a reverse transcriptase-inhibiting but non-toxic amount of a before-described adenosine derivative. The before-mentioned particularly preferred 2-substituted ddA derivatives, 2-substituted ddA-1-N- oxides, and ddA-1-N-oxide beta-anomers are particularly preferred in this aspect of the invention, as are the before-mentioned particularly preferred alpha-2-substituted-2',3'-dideoxyadenosines, their 1-N-oxides and alpha-2',3'-dideoxyadenosine itself. Inhibition of replication of a RTDV can be assayed by any usual assay such as the p24 (gag) assay used herein for HIV, and the like as are well known.

In usual practice, those contacted cells are animal cells such as human T cells or monocyte-derived cells where HIV or HTLV are implicated, feline lymphocyte cells where FeLV is the retrovirus, murine lymphocytes or cells where a virus like Mo-MuLV is implicated. Plant cells can also be contacted as where a virus such as cauliflower mosaic virus is implicated. Animal cells are utilized as illustrative hereinafter.

The anti-retroviral adenine derivatives of the present invention are administered to the warm-blooded animal internally, e.g., parenterally, orally, or rectally as a suppository, in amount sufficient to inhibit replication of a reverse transcriptase-dependent virus (RTDV), such as HTLV, FeLV, HIV, or the like, or as a prophylactic measure when the animal has been, or may have been, exposed to a RTDV.

An alpha- or beta-anomer useful in a method of this invention is administered in a non-toxic amount. It is to be understood that toxicity is relative, particularly where an infection of a retrovirus is concerned since such infections are usually fatal to the infected organism.

Non-toxicity is therefore judged by usual standards for the organsim to be treated. Obviously, an amount of adenine derivative less than that which kills an uninfected, treated organism is utilized so that the effects of the treatment do not hasten death of the infected organism.

It must also be remembered, however, that chemotherapeutic and other treatments for otherwise fatal diseases often cause extreme temporary discomfort and temporary illness for the recipient. Thus, the amount administered is less than that which kills the treated recipient or otherwise causes permanent impairment of the recipient. More preferably, the amount administered does not induce nausea, vomiting or fever.

Serum concentration of the anti-retroviral agent of this invention during treatment is maintained in the range of about 0.1 micromolar (uM) to about 20 uM, preferably about 0.5 uM to about 10 uM. Continuous intravenous infusion is one preferred mode of administration; however, other modes of injection, such as intraperitoneal or intramuscular can be utilized as well. To maintain the desired serum concentration of the anti-retroviral agent, a range of doses can be employed depending upon the specific mode of administration, objective of the particular treatment, the particular compound being used, and like considerations.

For example, for continual intravenous infusion the daily dose can be about 1 to about 50 milligrams per kilogram of body weight per day (mg/kg/day), and more preferably at about 5 to about 20 mg/kg/day, the dosage range being adjusted for optimum therapeutic response in the warm-blooded animal being treated. Similarly, for oral administration, the daily dose can be about 1 to about 50 mg/kg/day, and more preferably about 5 to about 20 mg/kg/day. In general, the amount of active anti-retroviral agent administered can vary over a relatively wide range to provide the desired serum concentration.

Unit dosage forms of the anti-retroviral agent can contain about one milligram to about 50 milligrams thereof.

To treat an acute RTDV infection, the aforementioned serum concentrations are maintained preferably for a time period of at least about 14 days. For a prophylactic treatment, the serum concentrations are maintained preferably for a time period of at least about 2 days, more preferably for about 3 to about 5 days.

For therapeutic use, the anti-retroviral agent of the present invention can be administered in the form of conventional pharmaceutical compositions. Such compositions can be formulated so as to be suitable for oral or parenteral administration, or as suppositories. In these compositions, the active ingredient can be combined in admixture with a pharmacologically acceptable carrier. The pharmacologically acceptable carrier can take a wide variety of forms depending upon the preparation desired for administration and the intended route of administration.

As an example, the compounds of the present invention can be utilized in liquid compositions such as sterile suspensions or solutions, or as isotonic preparations containing suitable preservatives. Particularly well suited for the present purposes are injectable media constituted by aqueous injectable isotonic and sterile saline or glucose solutions. Additional liquid forms in which the present compounds can be incorporated for administration include flavored emulsions with edible oils such as cottonseed oil, sesame oil, coconut oil, peanut oil, and the like, as well as elixirs and similar pharmaceutical vehicles.

The present anti-retroviral agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the anti-retroviral agent, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

The present compounds can also be used in compositions such as tablets or pills. To this end, the antiviral agent is mixed with conventional tabletting ingredients such as corn starch, lactose, sucrose, sorbitol, talc, stearic acid, magnesium stearate, dicalcium phosphate, gums, or similar materials as non-toxic, pharmacologically acceptable diluents or carriers. The tablets or pills of the present novel compositions can be laminated or otherwise compounded to provide unit dosage forms affording prolonged or delayed action.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate, and the like. A particularly suitable enteric coating comprises a styrene-maleic acid copolymer together with known materials that contribute to the enteric properties of the coating.

The term "unit dosage form," as used herein, refers to physically discrete units suitable as unitary dosages for administration to warm blooded animals, each such unit containing a predetermined quantity of the anti-retroviral agent calculated to produce the desired therapeutic effect in association with the pharmacologically acceptable diluent or carrier. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

As noted earlier, a compound of the present invention can be administered in conjunction with another drug or drugs such as AZT or ddC. When so administered, the concentration of the other drug and that more preferred for a compound of this invention can be lessened from those normally used. Typical dosages for such combined therapies utilize about 20 to about 50 percent of the dose required for a single agent when used alone.

C. Exemplary Results and Discussion

The beta-2-halo2',3'-dideoxyadenosine (2-halo-ddA) compounds and beta2',3'-dideoxyadenosine-1-N-oxide (ddA-1-0) are among the particularly preferred compounds of the several aspects of this invention, and are utilized hereinafter as exemplary of the class of both the alpha- and beta-anomers.

1. Metabolism of 2-halo2',3'-dideoxyadenosines

The beta-2-halo derivatives of beta-2',3'-dideoxyadenosine (2-halo-ddA) were extremely poor substrates for calf intestine adenosine deaminase. As indicated in Table 1, below, the $V_{max}$ values were equal to or less than 5 percent of the values for 2-'deoxyadenosine or 2',3'-dideoxyadenosine, but were greater in each case than the $V_{max}$ values for the corresponding 2-halo-2'-deoxyadenosine derivatives.

TABLE[1]

Metabolism of 2',3'-Dideoxyadenosine Derivatives by Adenosine Deaminase

| Compound | $Km^2$ | $Vmax^3$ | Relative Efficiency[4] |
|---|---|---|---|
| 2'-deoxyadenosine | 25 | 253.0 | 14.00 |
| 2',3'-dideoxyadenosine | 100 | 352.0 | 3.52 |
| 2-fluoro-2'-deoxyadenosine | 125 | 3.4 | 0.03 |
| 2-fluoro-2',3'-dideoxyadenosine | 180 | 14.5 | 0.08 |
| 2-chloro-2'-deoxyadenosine | 200 | 6.1 | 0.03 |
| 2-chloro-2',3'-dideoxyadenosine | 260 | 10.1 | 0.04 |
| 2-bromo-2'-deoxyadenosine | 200 | 1.2 | 0.06 |
| 2-bromo-2',3'-dideoxyadenosine | 333 | 8.1 | 0.24 |

[1]The indicated nucleosides at concentrations from 5-200 uM were incubated at 18-20° C. with 0.01 EU/ml calf intestinal adenosine deaminase in 10 mM sodium phosphate, pH 7.5. Deamination was monitored spectrophotometrically at 265 nanometers (nm) and 250 nm, as described hereinafter.
[2]Km is in micromolar (uM) units.
[3]Vmax is in units of micromoles per milligram minute (umoles × mg$^{-1}$ × min$^{-1}$).
[4]The ratio of Vmax/Km was used to determine the relative efficiencies of deamination.

The relative efficiencies of deaminaton, estimated by the ratio Vmax/Km, were about two order of magnitude smaller than the calculated value for 2'-deoxyadenosine. That two orders of magnitude difference is utilized herein to define a compound that is substantially free of deamination by adenosine deaminase under the conditions described herein.

The metabolism of 2-chloro-2',3'-dideoxyadenosine in viable T lymphoblasts was examined in detail, and was compared to that of 2',3'-dideoxyadenosine. Extracts of wild type CEM cells that had been incubated with 3 uM [8-$^3$H]-2-chloro-2',3'-dideoxyadenosine for 4 hours were fractionated by ion exchange high performance liquid chromatography (HPLC). Detected radioactive peaks corresponded to the free deoxynucleoside and to the 5'-mono-, di- and tri-phosphates, respectively. The total intracellular 2-chloro-2',3'-dideoxynucleotide content was 30 pmols/$10^8$ cells. The identity of the peaks was confirmed by enzymatic dephosphorylation, and reverse phase HPLC in the presence of authentic 2-chloro-2',3'-dideoxyadenosine.

As shown in Table 2, below, the deoxycytidine kinase deficient CEM variant accumulated only about 20 percent as much 2-chloro-2',3'-dideoxyadenosine phosphates as wild type CEM cells, under the same culture conditions. In contrast, when assayed under the same conditions 2',3'-dideoxyadenosine uptake was similar in the wild type T cells and the deoxycytidine kinase deficient variant (approximately 20-30 pmols/$10^8$ cells in each case).

TABLE 2[1]

Phosphorylation of 2-Chloro-2',3'-Dideoxyadenosine by Human T Cells

| CEM T Cell Line | Nucleotide Formed (pmols/$10^8$ cells/4 hrs) | | |
|---|---|---|---|
| | Monophosphate | Diphosphate | Triphosphate |
| Wild Type | 3.0 | 2.8 | 24.3 |
| Deoxycytidine kinase deficient | 1.7 | 0.8 | 3.4 |
| Deoxycytidine kinase and adenosine kinase deficient | 0.9 | 0.7 | 2.5 |

[1]Human CEM T cells, or variants deficient in either deoxycytidine kinase, or deoxycytidine kinase plus adenosine kinase, were incubated at a density of 5 × 10$^7$ cells/ml in medium containing 3 uM [8-$^3$H]-2-chloro-2',3'-dideoxyadenosine. After 4 hours, the nucleotides in the methanol-soluble extracts were determined after separation by HPLC, as described in the Materials and Methods.

Similar phosphorylations occur with the other compounds of this invention. These compounds can thus be said to be substrates for adenosine kinase, as well as substrates for deoxycytidine kinase.

The metabolites in the medium of CEM cell cultures that had been incubated with radiolabelled 2-chloro-2',3'-dideoxyadenosine, or with 2',3'-dideoxyadenosine, were also quantitated. The CEM cells did not significantly deaminate [8-$^3$H]-2-chloro-2',3'-dideoxyadenosine. Under the same condition, only about 2 percent of [2',3'-$^3$H]-2'3'-dideoxyadenosine remained in the medium after 4 hours culture. Analysis of the medium by thin layer chromatography (TLC) and HPLC revealed [2',3'-$^3$H]-2',3'-dideoxyinosine and a radioactive peak that co-eluted with [2',3'-$^3$H]-2',3'-dideoxyribose. These results are shown in Table 3, below.

TABLE 3[1]

Catabolism of 2-Chloro-2',3'-Dideoxyadenosine and 2',3'-Dideoxyadenosine by T Lymphoblasts

| Compound[2] | Addition | Catabolism (pmols/hr) $10^8$cells |
|---|---|---|
| 2-Cl-ddA | none | 40 |
| ddA | none | 240 |
| ddA | 2'-deoxycoformycin (5 uM) | 775 |
| ddA | coformycin (50 uM) | 100 |

TABLE 3[1]-continued

Catabolism of 2-Chloro-2',3'-Dideoxyadenosine
and 2',3'-Dideoxyadenosine by T Lymphoblasts

| Compound[2] | Addition | Catabolism (pmols/hr) $10^8$ cells |
|---|---|---|
| ddI | none | 800 |

[1]Human CEM T lymphoblasts at a density of 2 × $10^7$ cells/ml were incubated for 4 hours at 37 degrees C. with either 3 uM [8-$^3$H]-2-chloro- 2',3'-dideoxyadenosine, or 2 uM [2',3'-$^3$H]-2',3'-dideoxyadenosine or 2 uM [2',3'-$^3$H]-2',3'-dideoxyinosine. Then the dideoxynucleosides in the cultures were quantitated after separation by HPLC. In these studies, the intracellular dideoxynucleotide content after 4 hours was approximatedly 30 pmols/$10^8$ cells for both 2-chloro-2',3'-dideoxyadenosine and 2',3'-dideoxyadenosine.
[2]2-Cl-ddA = 2-chloro-2',3'-dideoxyadenosine; ddA = 2',3'-dideoxyadenosine; and ddI = 2',3'-dideoxyinosine.

As shown in Table 3, the specific adenosine deaminase inhibitor 2'-deoxycoformycin only partially inhibited the catabolism of 2',3'-dideoxyadenosine by the T cell cultures. However, coformycin, which inhibits both adenosine deaminase and AMP deaminase [Fishbein et al., *Biochem Med* 26:377-386 (1981)], prevented 2',3'-dideoxyadenosine degradation to both 2',3'-dideoxyinosine and 2'3'-dideoxyribose These results suggest that 2',3'-dideoxyadenosine may be deaminated directly, or after conversion to the 5'-monophosphate, and that 2',3'-dideoxyinosine. 5'-monophosphate may be dephosphorylated and released in the medium as 2',3'-dideoxyinosine, or broken down further to hypoxanthine and 2,3-dideoxyribose. The data thus emphasize the marked difference between the metabolism of 2',3'-dideoxyadenosine and its 2-chloro derivative.

2. Effects on HIV infection

The anti-HIV activities of the 2-halo-2',3'-dideoxyadenosine derivatives were first assayed in human MT-2 T lymphoblasts, as this system readily permitted a differentiation between anti-retroviral and anti-proliferative effects Exposure of the MT-2 T cell line to cell-free HIV led to the formation of syncytia within 4-5 days, and to a parallel decline in cell viability.

As shown in FIG. 1, contacting the MT-2 cells with 2-fluoro-, 2-chloro-, or 2-bromo-2',3'-dideoxyadenosine (each at 10 uM), wherein the cell medium constituted the pharmacologically acceptable carrier, blocked syncytia formation. In contrast, none of the corresponding 2-halo-2',3'-dideoxyinosine derivatives, nor the 2-halo-2'-deoxyadenosine congeners, at concentrations of 20 uM and 1 uM respectively, blocked HIV-induced syncytia formation FIG. 2 shows the relationship between the anti-HIV activities of the 2-halo-2',3'-dideoxyadenosine derivatives in MT-2 T lymphoblasts and the effects of the compounds on the growth of CEM T cells Generally, contacting the cells with an aqueous composition of a pharmacologically acceptable carrier containing a 2-halo-2',3'-dideoxynucleoside inhibited cell proliferation by about 50 percent at concentrations approximately two-fold higher than those that blocked HIV-induced syncytia formation. However, cultures that were supplemented with the 2-halo-2',3'-dideoxynucleoside composition were clearly protected from virus-induced cell killing.

Similar studies using MT-2 cells were also carried out with the known anti-retroviral compound ddA, and with ddA-N-oxide, a compound useful herein. The results of those studies showed ddA to inhibit the cytopathic effect of HIV and therefore also replication of the virus in those cells. 2',3'-Dideoxyadenosine-N-oxide (ddA-N-oxide) provided results similar to those of ddA.

The deoxycytidine kinase deficient mutant of the CEM cell line was at least 10-20 fold more resistant than parental cells to growth inhibition by the 2-halo-2',3'-dideoxyadenosine derivatives (FIG. 2). Furthermore, as shown by p24 (gag) antigen detection, neither 2-chloro-2',3'-dideoxyadenosine nor 2-bromo-2',3'-dideoxyadenosine protected the deoxycytidine kinase deficient variant from HIV infection (FIG. 3). It is notable that 2',3'-dideoxyadenosine exerted equivalent anti-HIV activity in wild type CEM cells and the deoxycytidine kinase deficient variant.

The activities of 2-halo-2',3'-dideoxyadenosine (2-F-,2-Cl- or 2-Br-ddA) derivatives were compared to those of 2-fluoro- and 2-chloro-2',3'-dideoxyinosine (2-F- and 2-Cl-ddI) and 2',3-dideoxyadenosine (ddA) against HIV-infected, antigen ELISA assay described herein.

The PHA-stimulated lymphocytes were suspended in media containing cell-free HIV, and were incubated overnight (about 18 hours). The cells were thereafter pelleted resuspended in a growth medium as pharmacologically acceptable carrier containing one of the above compounds at a 10 uM concentration, or with no added compound as a control, and plated at $10^5$ cells per microculture; the medium was also supplemented with interleukin-2. The release of virus into the supernate was measured by ELISA at 4, 8 and 12 days, post-inoculation. Each microculture plate also contained ten virus-free cultures that served as further controls. Ten cell cultures were used for each compound.

Cultures were scored positive if the optical density in the ELISA ($OD_{490}$) was greater than two standard deviations above the readings for the virus-free cultures. This method is adapted from that of McDougal et al. (1985) *J. Immunol.* 135:3151.

Cultures contacted with 2-F-ddA showed no positives through 8 days of culture, and 30 percent positives on day 12. 2-Br-ddA-containing cultures showed no positives on day 4, 20 percent positives on day 8, and 70 percent positives on day 12. ddA showed no positives at day 4, with 100 percent positives thereafter. All controls behaved as expected, and were 100 percent positive at all examinations (no additive +virus), or contained no positives at any examination (no virus).

The above results illustrate the unexpected improvement in inhibiting HIV replication of the present compounds as compared to ddA. As can be seen from those results, in this assay, ddA provided inhibition for a time period of only about four days. 2-F-ddA and 2-Br-ddA provided the same good protection over that four day time period, and also continued to provide some inhibition for the full twelve days of the assay. Mitsuya et al. (1987) *Nature*, 325:773-778 indicated that ddA is particularly effective in inhibiting replication of HIV in H9 and ATH8 T cells using the same amount of ddA and a culture period of nine days.

The before-discussed investigations of the metabolism of 2-halo-2',3'-dideoxyadenosine derivatives in human T lymphoblastoid cell lines have revealed interesting differences from 2',3'-dideoxyadenosine. The 2-chloro, 2-bromo and 2-fluoro derivatives of 2',3'-dideoxyadenosine were very resistant to deamination by purified adenosine deaminase. Indeed, viable human T cells did not significantly catabolize radiolabelled 2-chloro-2',3'-dideoxyadenosine, but converted the nucleoside to it 5'-mono-, di-, and triphosphate derivatives. The 2-halo-2',3'-dideoxyadenosine analogs inhibited the cytopathic effects of HIV toward the MT-2 T lymphoblastoid cell line, and also blocked the replication of HIV in CEM T lymphocytes, as measured by a p24 (gag) antigen capture assay.

Deoxycytidine kinase was the main enzyme catalyzing the phosphorylation of the 2-halo-2',3'-dideoxyadenosine derivatives, at least in T lymphocytes. Thus, a deoxycytidine kinase deficient variant of the CEM human T lymphoblastoid cell line accumulated much less 2-chloro-2',3'-dideoxyadenosine nucleotide than did wild type T cells. The deoxycytidine kinase deficient mutant was also resistant to the anti-proliferative effects of the three 2-halo-2',3'-dideoxyadenosine derivatives.

Increasing the size of the halogen substituent at C-2 position of the adenine ring diminished the antiproliferative action of the 2-substituted-2',3'-dideoxynucleosides without a concomitant reduction of anti-HIV activity. The Van der Waals radii of fluorine, chlorine and bromine are 1.35, 1.80 and 1. 95 Å respectively The increase in steric hindrance imposed by large size C-2 substituents shifts the equilibrium between the syn- and anti-nucleoside conformations, which in turn may exert an effect on nucleotide binding sites. Thus, the 2-substituted $C_1-C_6$ lower alkyl groups of the compounds of this invention whose Van der Waals radii begin with about 2.0 Å for methyl provide still further shifts in that conformation equilibrium.

In contrast to the 2-halo-2',3'-dideoxyadenosine derivative, 2',3'-dideoxyadenosine itself had equivalent anti-HIV activity in wild type CEM T cells, and in the deoxycytidine kinase deficient mutant. In this regard, 2',3'-dideoxyadenosine has been reported to be a substrate for adenosine kinase [Cooney et al. (1987), *Biochem. Pharm.* 36:1765-2768], and preliminary evidence from this laboratory suggests that cytoplasmic 5'-nucleotidase can also mediate the phosphorylation of 2',3'-dideoxyadenosine.

The exact biochemical basis for the anti-HIV activity of the useful 2',3'-dideoxyadenosine nucleotides remains to be determined. Most likely, the 5'-triphosphates are chain terminating substrates for the retroviral reverse transcriptase. However, it is also possible that the formation of the appropriate 2',3'-dideoxyadenosine 5'-monophosphates interferes with HIV replication in T cells. The failure of the 2-halo-2',3'-dideoxyadenosine derivatives to inhibit HIV replication in the deoxycytidine kinase deficient CEM mutant indicates that these compounds exert an anti-viral effect only after their phosphorylation.

The different routes of metabolism of the 2-halo-2',3'-dideoxyadenosine derivatives, compared to 2',3'-dideoxyadenosine have several implications concerning potential in vivo chemotherapy with the dideoxynucleosides. The amount of deoxycytidine kinase is greatest in cells of hematopoietic origin, whereas adenosine kinase and 5'-nucleotidase are abundant in most all cell types [Carson et al. (1987) *Proc. Natl. Acad. Sci. USA*, 74:5677-5681]. Thus, it seems likely that the tissue distribution and uptake of 2',3'-dideoxyadenosine and the 2-halo-2',3'-dideoxyadenosine derivatives could differ in vivo.

Although 2-chloro-2',3'-dideoxyadenosine was not catabolized significantly by human T cells, 2',3'-dideoxyadenosine was converted to 2',3'-dideoxyinosine, even in the presence of the specific adenosine deaminase inhibitor 2'-deoxycoformycin. Similar results were obtained by Cooney et al. (1987), *Biochem. Pharm.* 36:1765-2768]. The conversion was blocked by the AMP deaminase inhibitor coformycin, suggesting that deamination occurred at the 5'-monophosphate level, followed by dephosphorylation.

The failure of 2-chloro-2',3'-dideoxyinosine to accumulate in T cell cultures suggests that 2-chloro-2',3'-dideoxyadenosine 5'-monophosphate is not an efficient substrate for AMP deaminase. It is conceivable that differences in the rates of deamination of the 5'-monophosphates of 2',3'-dideoxyadenosine and its 2-halo derivatives are related to their contrasting effects on the growth of T lymphoblasts.

Mitsuya and Broder demonstrated that 2',3'-dideoxyinosine has in vitro anti-HIV activity that is nearly equivalent to 2',3'-dideoxyadenosine [Mitsuya et al. (1986) *Proc. Natl. Acad. Sci. USA*, 83:1911-1915], whereas Stoeckler et al. showed that 2',3'-dideoxyinosine is a substrate for purine *Biochemistry*, 19:102-108]. In accord with these data, the accumulation in the medium of a metabolite that co-eluted with $^3$H-2,3]-dideoxyribose after incubation of T cells with [2',3'-$^3$H]-2',3'-dideoxyadenosine was observed. The formation of the metabolite was blocked if the AMP deaminase inhibitor coformycin was included in the culture medium. These results suggest that catabolism of 2',3'-dideoxyinosine can occur in viable cells, and are in accord with recent data of Cooney et al. and co-workers [Cooney et al. (1987) *Biochem. Pharm.*, 36:2765-1768].

In cultured T lymphoblasts 2',3'-dideoxycytidine is a more potent inhibitor of HIV infection than 2',3'-dideoxyadenosine [Mitsuya et al. (1986) *Proc. Natl. Acad. Sci. USA*, 83:1911-1915]. As little as 0.1 uM of 2',3'-dideoxycytidine has been shown to block the replication and cytopathic effects of HIV in T lymphoblasts. Ten to fifty fold higher concentrations of 2',3'-dideoxyadenosine and of the 2-halo-2',3'-dideoxyadenosine derivatives were required to achieve a similar anti-HIV effect. The 2-halo-2',3'-deoxyadenosine derivatives were also more toxic to T cells than 2',3'-dideoxyadenosine. However, in vivo studies have indicated that 2-chloro-2'-deoxyadenosine has immunosuppressive and anti-leukemic activity at concentrations that do not severely affect other bone marrow elements [Carson et al. (1984) *Proc. Natl. Acad. Sci. USA*, 81:2232-2236].

MATERIALS AND METHODS

A. Materials

The serum and culture media came from Grand Island Biological Co. (Grand Island, N.Y.). Deoxycoformycin was supplied by Warner-Lambert/Parke-Davis (Detroit, Mich.), and coformycin by Boehringer (La Jolla, Calif.). Unless otherwise stated, all other reagents came from Aldrich (Milwaukee, Wis.).

B. Nucleoside Synthesis

2-Chloroadenine and 2-bromoadenine were prepared by treatment of 2,6-dichloropurine [Brown et al. (1958) *J. Org. Chem.* 23:125-127] or 2,6-dibromopurine [Montgomery et al. (1968) in Synthetic Procedures in Nucleic Acids Chemistry (Tipson et al. eds) 180-182 John Wiley and Sons, New York] with dry methanolic ammonia. 2-Fluoroadenine [Montgomery et al. (1960). *J. Am. Chem. Soc.*, 82:463-468]and one sample of 2-bromoadenine were kindly provided by Dr. J. A. Montgomery (Southern Research Institute, Birmingham, Ala.).

The 2-halo-2'-deoxynucleosides were prepared by transfer of the deoxyribose moiety from thymidine to the respective purine base, using a partially purified transdeoxyribosylase from *Lactobacillus helveticus* American Type Culture Collection, Rockville, Md., (ATCC 8018), as described previously [Carson et al. (1980) *Proc. Natl. Acad. Sci. USA*, 77:6865–6869].

The 2-halo- (fluoro-, chloro-, bromo-) 2',3'-dideoxyadenosines were generated from the corresponding 2-halo-2'-deoxynucleosides by Barton elimination of the 3'-OH group as described by Robins et al. (1983) *J. Am. Chem. Soc.*, 105, 4059–4065. The products were purified to homogeneity by preparative reverse phase HPLC on a Waters $C_{18}$ uBondapak column eluted with a 0–10 percent acetonitrile gradient in water.

The 2-halo-ddA compounds were more specifically prepared as follows.

5'-dimethoxytrityl derivatives of 2-halo-2'-deoxyadenosines were obtained by reacting 1 equivalent of parent compound (previously dried by evaporation from pyridine) with 1.2 equivalents of 4,4'-dimethoxytrityl chloride in pyridine. The reaction was followed by TLC on silica gel in methanol/methylene chloride (1/9; v/v). After 2 hours, pyridine was evaporated, and the reaction product was dissolved in ethyl acetate and extracted with a saturated solution of NaCl. After several extractions of the water phase with ethyl acetate, ethyl acetate fractions were pooled, dried with $MgSO_4$, ethyl acetate was evaporated and the product was dissolved in acetonitrile.

5'-dimethoxytrityl-2-halo-2'-deoxynucleosides were reacted with 1.1 equivalents of phenyl chlorothionocarbonate in freshly distilled acetonitrile using 5 equivalents of 4-dimethylaminopyridine as catalyst. Reactions proceeded for 12 hours in room temperature. Product Rf on silica gel TLC in methanol/methylene chloride (1/9)=0.7.

The 5'-OH group of 5'-dimethoxytrityl-3'-phenylthiocarbonate-2-halo-adenosine was deblocked with 80 percent acetic acid (1 hour reaction time). Acetic acid was removed under vacuum, the residue was extracted with ethyl acetate followed by washing of the organic phase with saturated bicarbonate and then saturated NaCl. Ethyl acetate was removed under vacuum. Product Rf on silica gel TLC in methanol/methylene chloride (1/9)=0.375.

The 3'-phenylthiocarbonyl-2-halo-2'-deoxyadenosines were suspended in toluene and 0.2 equivalents of 2,2'-azobis(2-methylpropionitrile) were added. The reaction flask was purged with nitrogen for 30 minutes, and then placed in the oil bath at 80 degrees C. After 10 minutes at 80 degrees C, 1.5 equivalents of tributylthin hydride were added. The reduction proceeded for 4 hours with continuous nitrogen purge.

After cooling to the room temperature, the reaction mixture was extracted several times with water. Water fractions were pooled and lyophilized. Reaction product 2-halo-2',3'-dideoxyadenosines were purified by preparative layer chromatography (PLC) on silica gel in the methanol/methylene chloride elution system. Values of Rfs on silica gel TLC in methanol/methylene chloride 1/9 for 2',3'-dideoxyadenosine (prepared similarly), 2-fluoro-2',3'-dideoxyadenosine, 2-chloro-2',3'-dideoxyadenosine, and 2-bromo-2',3'-dideoxyadenosine were 0.1, 0.12, 0.16 and 0.2, respectively.

All the synthesized 2',3'-dideoxynucleosides showed characteristic purple color after staining with diphenylamine. This particular staining appears specific to 2',3'-dideoxyfuranose compounds. The Rf values followed the same pattern during chromatography on C18 HPLC column (isocratic gradient of 7.5 percent acetonitrile in water). The products showed single spots by TLC using either methanol/methylene chloride (1/9,v/v) or ethyl acetate/methylene chloride (1/1,v/v) as elutant, and depending on batch the appeared to be 99.0–99.9 percent pure by HPLC.

The 100 MHz NMR spectra of the 2-halo-2',3'-dideoxyadenosine nucleosides in $d_6$-DMSO showed the elimination of the doublet corresponding to the 3'-hydroxyl group proton (at about 5.25 ppm) and additional peaks due to changed 2'-3' proton coupling. Additional confirmation of structure was supplied by chemical ionization mass spectroscopy.

Exemplary 100 MHz spectra using TMS as an internal standard for 2-F-ddA and 2-Cl-ddA provided the following peaks in ppm downfield from TMS.

2-F-ddA: 1.78 m (1H; 2'H); 2.10 m (1H; 2'H); 3.15 m (3H; 5'H's and 4'H); 3.84 m (1H; 3'H); 4.70 t (1H; 5'OH); 5.92 t (1H;); 7.60 s (NH); and 8.10s (1H, 8H).

2-Cl-ddA: 1.78 m (1H; 2'H); 2.18 m (1H; 2'H); 3.25 m (3H; 5'H's and 4'H); 3.94 m (1H; 3'H); 4.68 t (1H, 8H). OH); 5.92 t (1H; 1'H); 7.56 s (NH); and 8.18 s (1H, 8H).

In the above list: m=multiplet; t=triplet and s=singlet. The first designation indicates the number of hydrogens involved in the peak, whereas the second, underlined designation indicates which hydrogen is thought to have given rise to that peak.

To generate the 2-halo-2',3'-dideoxyinosine derivatives, the 2-halo-2',3'-dideoxyadenosine congeners at 100–200 uM were incubated for 3–7 days with at least 1,000 EU/ml of calf intestinal adenosine deaminase (Sigma, St. Louis) at 37 degrees C. The reactants and products were separated by reverse phase HPLC on a Waters $C_{18}$ uBondapak column eluted with 5 percent acetonitrile in water.

[2',3'-$^3$H]-2',3'-dideoxyribose-1-phosphate was produced by incubation of [2',3'-$^3$H]-2',3'-dideoxyinosine with purine nucleoside phosphorylase and xanthine oxidase (Sigma, 1 EU/ml each) in 0.1 M potassium phosphate pH 6.0.

[8-$^3$H]-2-chloro-2',3'-dideoxyadenosine (sp. act. 11 GBq/nmol) and [2',3'-$^3$H]-2',3'-dideoxyadenosine (final sp. act. 167 GBq/nmol) were prepared by Moravek Biochemicals (Brea, Calif.).

As noted earlier, the 1-N-oxide compounds are readily prepared by the method of Klenow et al. (1961) *Biochem. Biophys. Acta*, 52:386–389, with slight modification. An exemplary synthesis using 2',3'-dideoxyadenosine is provided below. The other alpha- and beta-anomer 1-N-oxide compounds can be prepared similarly.

2',3'-Dideoxyadenosine [30 micromoles (umoles)] in 5 ml of NH at pH 5.5 was treated with 120 umoles of the magnesium salt of monoperphthalic acid at a temperature of zero degrees C with continuous mixing. After a time period of 12 hours, the mixture was lyophilized, dissolved in 2 ml of water and applied to the top of a 20 ml Dowex AG1X-8 (formate form). The 1-N-oxide was eluted with 0.1 M $NH_4CO_2$.

The resulting product exhibited a characteristic UV spectrum with a maximum at 232 nanometers. 2',3'-Dideoxyadenosine-1-N-oxide migrated as a single spot on silica gel TLC using methylene chloride/methanol (9/1, v/v) as solvent, and had an Rf value of 0.05.

C. Metabolism by Adenosine Deaminase

The individual nucleosides, at concentrations from 5–200 uM in 10 mM sodium phosphate, pH 7.5, were incubated at 18–20 degrees C. with 0.01 EU/ml calf intestinal adenosine deaminase. The change in the optical density at 265 nm and 250 nm was monitored spectrophotometrically. The Km and $V_{max}$ values were determined by the Lineweaver-Burke method, utilizing the $\Delta E_{265}{}^M$ between adenosine and inosine (8100), which was the same for the 2-halo-2',3'-dideoxyadenosine derivatives.

D. Metabolism in T Lymphoblastoid Cell Lines

The human T lymphoblastoid cell line, CCRF-CEM, and mutants deficient in either deoxycytidine kinase (clone AraC-8D), or deoxycytidine kinase plus adenosine kinase (clone AraC-8DM10-5) were obtained and propagated as described previously [Foley et al., (1965) *Cancer*, 18:552-529 and Hershfield et al., (1982) *J. Biol. Chem.*, 257:6380-6386]. For metabolic studies, the cells were cultured in RPMI 1640 medium supplemented with 2 mM L-glutamine and 10 percent fetal bovine serum at a density of $2 \times 10^7$ cells/ml in the presence of radiolabelled dideoxynucleosides, as indicated earlier. Some cultures were pre-incubated for 30 minutes either with 5 uM 2'-deoxycoformycin or 50 uM coformycin. After 4 hours of incubation the cells were harvested by centrifugation.

The cell pellets were washed with Hank's balanced salt solution at 4 degrees C., and extracted with 1 ml 60 percent methanol/water at −20 degrees C. for 10 minutes. Initial studies included 2',3'-dideoxyadenosine 5'-triphosphate as an internal recovery marker. The nucleotides were fractionated by high performance liquid chromatography on a Whatman Partisil-10 SAX column, applying a gradient of zero to 100 percent buffer B in buffer A. Buffer A was 7 mM potassium phosphate pH 3.4. Buffer B was 0.5 M potassium phosphate, pH 3.4, one M KCl. The flow rate was 1.5 ml/minute, 1 minute fractions were collected. Buffer A was used alone for the first ten fractions after which elution with Buffer B began and was continued through fraction thirty, after which the eluting buffer was completely Buffer B. The nucleoside was eluted by about fraction six. The monophosphate eluted between about fractions fifteen and eighteen, the diphosphate between about fractions twenty-seven and thirty-two, and the triphosphate eluted between about fractions fifty-one and about sixty-five.

For peak identification, the fractions corresponding to 2-chloro-2',3'-dideoxyadenosine 5'-mono-, 5'-di- and 5'-triphosphate were collected, desalted on a Sephadex G-10 column, and dephosphorylated with alkaline phosphatase and snake venom phosphodiesterase, as described in Hershfield et al. (1982) *J. Biol. Chem.* 257:6380-6386. The resultant radiolabelled nucleosides were mixed with authentic 2-chloro-2',3'-dideoxyadenosine and separated by reverse phase HPLC on a $C_{18}$ uBondapak column that was eluted at a flow rate of 1 ml/minute with a 2-20% acetonitrile gradient in 5 mM potassium phosphate, pH 4.0.

The radioactive compounds in the culture medium were fractionated by thin layer chromatography. Ten microliter (ul) aliquots of medium were spotted directly on cellulose plates and developed with 1 M ammonium acetate pH 7.4. The Rf values were: 2-chloro-2',3'-dideoxyadenosine 0.30; 2',3'-dideoxyadenosine 0.35; 2-chloro-2',3'-dideoxyinosine 0.60; 2',3'-dideoxyinosine 0.65; 2,3'-dideoxyribose-1-phosphate 0.80, 2',3'-dideoxyribose 0.90. The respective spots were cut out and radioactivity was determined by liquid scintillation spectrometry. The identities of the spots were also confirmed by cochromatography of the radioactive counts with authentic compounds on a $C_{18}$ uBondapak column, that was eluted as described above.

E. Anti-HIV Activity

The MT-2 human lstoid cell line, which carries the human T cell leukemia virus type I (HTLV-1) genome, was used to assess the cytopathic effects of HIV, and the protective effects of the various nucleosides. Harada et al., [Harada et al (1985) *Science* 229:563-566], showed that infection of MT-2 cells with HIV leads to the appearance of multinucleate giant cells. The formation of syncytia, with resultant cell death, depends upon the expression on the cell-surface of the HIV envelope glycoproteins gp160, gp120, and gp41, by cells that bear the differentiation antigen CD4 (T4) [Lipson et al., (1986) *Nature*, 323:725-728].

In the reported studies, the formation of syncytia in the MT-2 cell line (provided by J. Riggs and M. Aschen, State Department of Public Health, Berkelye, CA) was a sensitive and reproducible system to follow both the course of HIV infection and the potential cytotoxic effects of the added nucleosides. HIV (strain LAV) maintained in CEM cell culture was obtained from F. Barre-Sinoussi, J. C. Chermann and L. Montagnier (Institute Pasteur, Paris).

Cell-free virus was prepared by mixing LAV-infected CEM cells with two liters of $2 \times 10^6$ cells/ml of uninfected CEM cells at a ratio of 1:20 and incubating at 37 degrees C. for six days at which time, more than 80 percent of the cells expressed the p24 (gag) antigen using mouse monoclonal antibody M33, obtained from F. Vernoese di Marzo and M. Sarngadharan (Litton Bionetics, Rockville, Md.) using an enzyme immunofiltration staining method [Cleveland et al. (1987) *J. Clin. Microbiol.*, 25:416-420]. The cells were centrifuged at $750 \times g$ for 10 minutes. The clarified supernatant was then titered by terminal dilution assay in 96 well microtiter plates containing $6 \times 10^4$ MT-2 cells per well suspended in a final volume of 200 ul RPMI 1640 medium containing 10 percent fetal bovine serum, 2 mM glutamine and 1 percent polybrene. Quadruplicate wells were inoculated with 20 ul of 10-fold dilutions of the virus pool, which had an infectivity titer of $10^8$ $TCID_{50}$/ml.

When HIV was added to this microtiter culture system at a multiplicity of infection of 0.1 $TCID_{50}$/cell, multinucleated giant cells appeared within 48 hours, and the majority of cells were fused in syncytia structures by day 4. The appearance of giant cells correlated with detectable antigens and RNA of HIV.

For measurement of antiviral activity, different concentrations of the assayed compounds were added to duplicate wells at the time of infection, and the cultures were incubated at 37 degrees C. After 4 and 5 days, the numbers of syncytia per culture were enumerated microscopically.

The results presented herein were confirmed in five separate experiments. Controls containing uninfected and infected cells with and without anti-retroviral nucleosides were included.

The results were expressed in semi-quantitative units that take into account the growth pattern of MT-2, and the ability of the HIV to cause both syncytia formation and cell death. In this unit system, 1 corresponds to 1-3 syncytia per well and no change in cell count compared to control cultures lacking virus; 2 corresponds to 3-10 syncytia per well and up to 20 percent cell death; 3 corresponds to 10–30 syncytia per well and a 20–70 percent drop in cell viability; 4 corresponds to more than 30 syncytia well and at least a 70 percent fall in the viable cell count.

HIV infection of the CEM T lymphoblastoid cell line was monitored by the release of the HIV p24 (gag) protein into the medium, exactly as described previously [Cleveland et al. (1987) *J. Clin. Microbiol.*, 25:416–420 and Fishbein et al. (1981) *Biochem. Med.*, 26:377–386]. The growth inhibiting effects of the nucleosides toward CEM lymphoblasts, and toward the deoxycytidine kinase deficient mutant, were also monitored as described earlier [Carson et al. (1980) *Proc. Natl. Acad. Sci. USA*, 77:6865–6869].

| Compositions for Administration In Vivo | |
|---|---|
| EXAMPLE A: IV Injectable Solution Concentrate | |
| Ingredient | Amount, % wt. vol. |
| anti-retroviral agent | 0.1 |
| benzyl alcohol NF | 0.9 |
| purified water | 100.0 |
| EXAMPLE B: Compressed Tablet | |
| Ingredient | Amount, mg/Tablet |
| anti-retroviral agent | 20 |
| dibasic calcium phosphate NF | q.s. |
| starch USP | 40 |
| modified starch | 10 |
| magnesium stearate USP | 1–5 |
| EXAMPLE C: Hard Shell Capsule | |
| Ingredient | Amount, mg/Capsule |
| anti-retroviral agent | 10 |
| lactose, spray dried | q.s. |
| magnesium stearate | 1–10 |
| EXAMPLE D: Oral Liquid (Syrup) | |
| Ingredient | Amount, % wt./vol. |
| anti-retroviral agent | 50.0 |
| liquid sugar | 75.0 |
| methyl paraben USP | 0.18 |
| propyl paraben USP | 0.02 |
| flavoring agent | q.s. |
| purified water, q.s. ad | 100.0 |

The anti-retroviral agent in the above compositions can be any of the before-described compounds. However, the IV intravenous injectable solution preferably contains an alpha- or beta-2-halo-2',3'-dideoxyadenosine, 2-methyl-2',3'-dideoxyadenosine or a corresponding 1-N-oxide, as well as alpha-2',3'-dideoxyadenosine, and alpha- or beta-2',3'-dideoxyadenosine-1-N-oxide. The compositions of Examples B-D preferably contain a beta-2-halo- or 2-methyl-2',3'-dideoxy-2'haloarabinofuranosidyl adenosine, or a corresponding 1-N-oxide, again including the beta-2',3'-dideoxyadenine-1-N-oxide derivative, with a 2'-fluoro compound being particularly preferred.

The present invention has been described with respect to preferred embodiments. It will be clear to those skilled in the art that modifications and/or variations of the disclosed subject matter can be made without departing from the scope of the invention set forth herein.

What is claimed is:

1. A substituted adenine bonded beta-9,1' to a furanosidyl ring and having a structure that corresponds to the formula

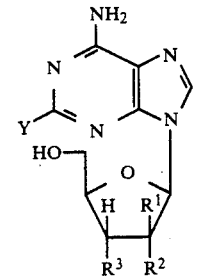

where
Y is a halogen selected from the group consisting of fluoride, chloride and bromide; and
$R^1$, $R^2$ and $R^3$ are H.

2. The substituted adenine of claim 1 wherein Y is chloro.

3. The substituted adenine of claim 1 wherein Y is fluoro.

4. The substituted adenine of claim 1 wherein Y is bromo.

5. A composition comprising a pharmaceutically acceptable carrier containing an about 0.1 to about 20 micromolar amount of a substituted adenine of claim 1.

* * * * *